(12) United States Patent
Otake et al.

(10) Patent No.: US 10,641,845 B2
(45) Date of Patent: May 5, 2020

(54) HIGH FREQUENCY COIL AND MAGNETIC RESONANCE IMAGE PICKUP DEVICE

(71) Applicant: Hitachi, Ltd., Tokyo (JP)

(72) Inventors: Yosuke Otake, Tokyo (JP); Hisaaki Ochi, Tokyo (JP); Kohjiro Iwasawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 547 days.

(21) Appl. No.: 15/504,681

(22) PCT Filed: Aug. 7, 2015

(86) PCT No.: PCT/JP2015/072536
§ 371 (c)(1),
(2) Date: Feb. 17, 2017

(87) PCT Pub. No.: WO2016/035510
PCT Pub. Date: Mar. 10, 2016

(65) Prior Publication Data
US 2017/0254864 A1    Sep. 7, 2017

(30) Foreign Application Priority Data

Sep. 5, 2014  (JP) ................................. 2014-181324

(51) Int. Cl.
*G01R 33/34* (2006.01)
*G01R 33/36* (2006.01)
(Continued)

(52) U.S. Cl.
CPC .............. *G01R 33/34* (2013.01); *A61B 5/055* (2013.01); *G01R 33/3415* (2013.01);
(Continued)

(58) Field of Classification Search
USPC .......................... 324/300–322; 600/407–435
See application file for complete search history.

(56) References Cited

U.S. PATENT DOCUMENTS

| | | | | |
|---|---|---|---|---|
| 4,075,552 A | * | 2/1978 | Traficante | .......... G01R 33/3628 324/322 |
| 8,169,221 B2 | * | 5/2012 | Griswold | .......... G01R 33/3635 324/307 |

(Continued)

FOREIGN PATENT DOCUMENTS

WO    2011/122084 A1    10/2011

OTHER PUBLICATIONS

Roemer P.B. et al., "The NMR Phased Array", Journal of Magnetic Resonance, USA, 1990, 16, pp. 192-225.
(Continued)

*Primary Examiner* — G. M. A Hyder
(74) *Attorney, Agent, or Firm* — Mattingly & Malur, PC

(57) ABSTRACT

A technique for reconciling large sensitivity area and high sensitivity for deep part in a multi-channel array coil of an MRI apparatus without complicating the configuration, and realizing both higher speed imaging and high image quality is provided. An RF coil (array coil) of a magnetic resonance imaging apparatus comprising a plurality of subcoils is provided. At least one of the subcoils is a first subcoil of which resonance frequency as that of the subcoil alone differs from magnetic resonance frequency. The first subcoil is adjusted so that it magnetically couples with a second subcoil, which is at least one other subcoil, and thus resonates at the same frequency as the magnetic resonance frequency. Input and output terminals of the first subcoil and the second subcoil are connected to different low input and output impedance signal processing circuits, respectively.

10 Claims, 18 Drawing Sheets

(51) Int. Cl.
    *A61B 5/055*     (2006.01)
    *G01R 33/3415*     (2006.01)
    *G01R 33/3815*     (2006.01)
    *G01R 33/54*     (2006.01)

(52) U.S. Cl.
    CPC ..... *G01R 33/34076* (2013.01); *G01R 33/365* (2013.01); *G01R 33/3635* (2013.01); *G01R 33/3642* (2013.01); *G01R 33/3657* (2013.01); *G01R 33/3815* (2013.01); *G01R 33/54* (2013.01)

(56) References Cited

U.S. PATENT DOCUMENTS

| | | | | |
|---|---|---|---|---|
| 8,198,894 | B2* | 6/2012 | Kaneko | G01R 33/34046 324/307 |
| 10,520,564 | B2* | 12/2019 | Otake | A61B 5/0555 |
| 2008/0297154 | A1* | 12/2008 | Otake | G01R 33/34046 324/318 |
| 2009/0134876 | A1* | 5/2009 | Griswold | G01R 33/3415 324/318 |
| 2009/0230965 | A1* | 9/2009 | DeVries | G01R 33/3403 324/322 |
| 2009/0251145 | A1* | 10/2009 | Kaneko | G01R 33/34046 324/318 |
| 2011/0031970 | A1* | 2/2011 | Ninomiya | A61B 5/055 324/309 |
| 2013/0069652 | A1 | 3/2013 | Otake et al. | |
| 2016/0216345 | A1* | 7/2016 | Greim | G01R 33/3642 |
| 2018/0180690 | A1* | 6/2018 | Otake | A61B 5/055 |
| 2019/0041476 | A1* | 2/2019 | Otake | G01R 33/34076 |

OTHER PUBLICATIONS

Klaas P.P. et al., "SENSE: Sensitivity Encoding for Fast MRI", Journal of Magnetic Resonance, USA, 1999, 42, pp. 952-962.

B. Wu, "Capacitor/Inductor Decoupling and Its New Application to Microstrip Array", International Society for Magnetic Resonance in Medicine, 2011, pp. 1860.

Nikolai I. Avdievich, "Novel Inductive Decoupling for Single-and Double-Tuned Transceiver Phased Arrays to compensate for both Reactive and Resistive Components of the Mutual Impedance", International Society for Magnetic Resonance in Medicine, 2012, pp. 2806.

International Search Report of PCT/JP2015/072536 dated Nov. 2, 2015.

International Preliminary Report on Patentability received in corresponding International Application No. PCT/JP2015/072536 dated Mar. 16, 2017.

* cited by examiner (a)

(b)

(c)

(a)

(b)

(a)

(b)

(c)

(a)

(b)

HIGH FREQUENCY COIL AND MAGNETIC RESONANCE IMAGE PICKUP DEVICE

TECHNICAL FIELD

The present invention relates to a magnetic resonance imaging (MRI) apparatus, in particular, an RF coil (Radio Frequency Coil, high-frequency coil) for irradiating a radio frequency magnetic field and detecting a magnetic resonance signal.

BACKGROUND ART

MRI apparatuses are imaging apparatuses for imaging an arbitrary section of an imaging subject using the nuclear magnetic resonance phenomenon. Specifically, MRI apparatuses irradiate a radio frequency magnetic field on an imaging subject placed in a spatially uniform magnetic field (static magnetic field) to cause magnetic resonance, detect generated magnetic resonance signals, and perform image processing for the detected signals to obtain a tomographic image.

A device that irradiates a radio frequency magnetic field on an imaging subject and detects magnetic resonance signals generated from the imaging subject is called RF coil. The RF coil has a loop part (coil loop) for performing the irradiation and detection. If this coil loop is made smaller, sensitivity becomes higher, although sensitivity area becomes narrower. On the other hand, if the coil loop is made larger, the sensitivity area can be expanded. In this way, magnitude of sensitivity and size of sensitivity area of RF coil are in a trade-off relationship. Since magnetic resonance signals are signals of a rotating magnetic field generated in a direction perpendicular to the static magnetic field, it is preferred that the RF coil is disposed in such a direction that the RF coil can irradiate a magnetic field and detect signals in a direction perpendicular to the static magnetic field.

As described above, a smaller RF coil provides higher sensitivity, but shows narrower sensitivity area. As a means for solving this problem, there is a multi-channel array coil comprising a plurality of RF coils arranged in the form of array (refer to, for example, Non-patent document 1). Since multi-channel array coils show high sensitivity and wide sensitivity area, they constitute the current main stream of receiving RF coil. Each individual RF coil constituting a multi-channel array coil is henceforth referred to as subcoil.

If RF coils having the same resonance characteristics are disposed closely to each other, they usually interfere with each other by magnetic coupling. Since magnetic coupling degrades performances of the RF coils, it is essential to eliminate magnetic coupling between subcoils in a multi-channel array coil. Non-patent document 1 describes that magnetic coupling is reduced as far as possible by disposing the subcoils so that adjacent subcoils partially overlap with each other. Further, interference from subcoils other than the overlapping subcoils is reduced by using low input preamplifier, inductor, and capacitor so that a part of each coil loop has high impedance.

In recent years, high-speed imaging using difference of spatial sensitivities of individual subcoils of a multi-channel array coil (for example, refer to Non-patent document 2) is spreading. As for the high-speed imaging, a larger number of channels realize a higher imaging speed. Therefore, channel number of multi-channel array coil becomes further larger in recent years, and supermulti-channel array coils such as those of 32 channels or 128 channels are spreading at the present.

PRIOR ART REFERENCES

Non-Patent Documents

Non-patent document 1: Roemer P. B. et al., "The NMR Phased Array", Journal of Magnetic Resonance, USA, 1990, 16, pp. 192-225

Non-patent document 2: Klaas P. P. et al., "SENSE: Sensitivity Encoding for Fast MRI)", Journal of Magnetic Resonance, USA, 1999, 42, pp. 952-962

SUMMARY OF THE INVENTION

Object to be Achieved by the Invention

However, if individual subcoils constituting an array coil become smaller because of use of larger number of channels, depth of the sensitivity area of the whole array coil that should be an assembly of subcoils showing a narrow sensitivity area becomes smaller. Therefore, deep part sensitivity of a supermulti-channel array coil developed for high-speed imaging becomes lower compared with that of an array coil having fewer channels. Therefore, for a deep part of imaging subject, it is difficult to obtain a clear image.

Further, the elimination of magnetic coupling performed for realizing an array coil reduces magnetic coupling as far as possible, and does not completely eliminate magnetic coupling. Therefore, in a combination of subcoils disposed at a position where magnetic coupling strongly generates, not a little magnetic coupling remains, and performance of the array coil degrades.

In order to make such remaining magnetic coupling as small as possible, it is also possible to provide a plurality of magnetic coupling elimination means. However, such magnetic coupling elimination means themselves actually give a certain extent of loss. Therefore, if a plurality of magnetic coupling elimination means are provided, not only magnetic coupling is reduced, but also sensitivity of the array coil is reduced. In the case of a supermulti-channel array coil, it is necessary to remove magnetic coupling with a plurality of subcoils, and therefore configuration becomes complicated.

A multi-channel array coil is generally disposed so that a surface coil covers an imaging subject. However, in a case where direction of magnetic field produced by one subcoil that constitutes the array coil is almost the same as the direction of the magnetic field of the static magnetic field (in the case of tunnel type MRI apparatus where the direction of the static magnetic field is parallel to the ground, for example, parietal region of imaging subject etc., or in the case of open type MRI where the direction of the static magnetic field is perpendicular to the ground, for example, front or back abdominal surface, etc.), sensitivity area becomes narrower, and therefore signal receiving efficiency is degraded. In such a case, even if the number of the subcoils is increased to increase the number of channels, substantial sensitivity hardly increases.

The present invention was accomplished in light of the aforementioned circumstances, and provides a technique for realizing a large sensitivity area with high sensitivity for a deep part in a multi-channel array coil of an MRI apparatus without complicating the configuration, and thereby realizing higher imaging speed with higher image quality.

Means for Achieving the Object

The present invention provides an RF coil comprising a plurality of subcoils (array coil) for an MRI apparatus. At least one of the subcoils is a first subcoil of which resonance frequency as this subcoil alone differs from nuclear magnetic resonance frequency. The first subcoil is adjusted so that it is intentionally magnetically coupled with a second subcoil, which is at least one other subcoil, and thereby made to resonate at the same frequency as the nuclear magnetic resonance frequency. Input and output terminals of the first subcoil and the second subcoil are connected to different low input and output impedance signal processing circuits, respectively.

Effect of the Invention

According to the present invention, in an RF coil of an MRI apparatus, multi-channel characteristic is reconciled with a large and deep sensitivity area, and an image of high image quality can be obtained.

MODES FOR CARRYING OUT THE INVENTION

First Embodiment

The first embodiment of the present invention will be explained below. In the following descriptions, components having the same functions are referred to with the same numerals or codes in all the drawings for explaining the embodiments of the present invention, and repetition of explanations thereof is omitted.

[Configuration of MRI Apparatus]

Figure 1:
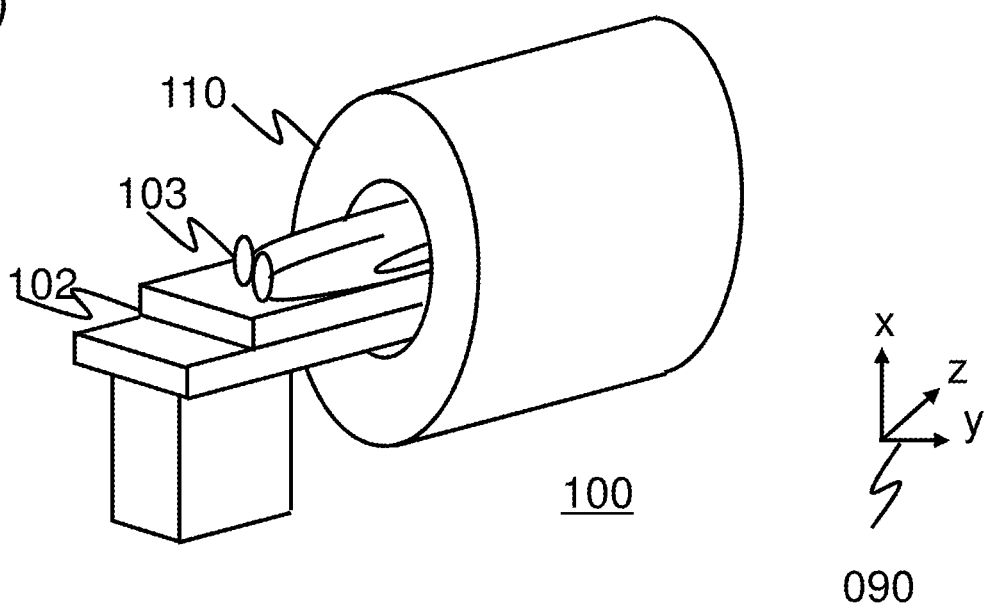
FIGS. 1a and 1b are conceptual views of MRI apparatuses of the first embodiment.
Figure 1:
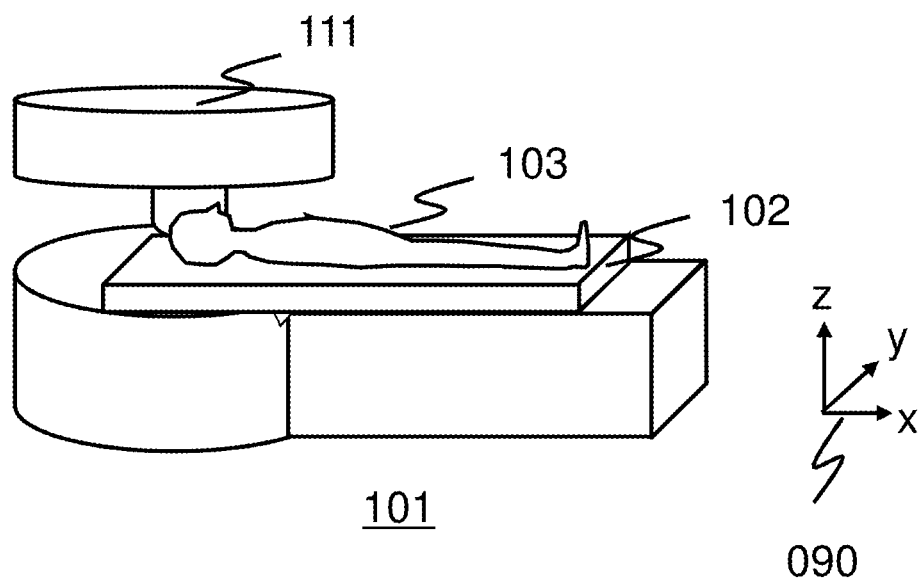

First, configuration of the whole MRI apparatus of this embodiment will be explained with reference to FIG. 1. FIG. 1 includes external views of MRI apparatuses of this embodiment. FIG. 1a shows an MRI apparatus 100 of the horizontal magnetic field type using a tunnel type magnet that generates a static magnetic field with a solenoid coil. FIG. 1b shows an MRI apparatus 101 of the vertical magnetic field type using hamburger type magnets, which comprises separate upper and lower magnets for enhancing spaciousness. These MRI apparatuses 100 and 101 comprise a table 102, on which a test subject 103 is placed. This embodiment can be applied to both the MRI apparatus 100 comprising a horizontal magnetic field type magnet 110, and MRI apparatus 101 comprising vertical magnetic field type magnets 111.

Explanations will be henceforth made for the MRI apparatus 100 having the horizontal magnetic field type magnet 110 as an example. For this embodiment, both types of the MRI apparatuses having such external views as mentioned above can be used. These are mere examples, and the MRI apparatus of this embodiment is not limited to these configurations. For this embodiment, various kinds of known MRI apparatuses can be used without particular restrictions concerning configuration or type of the apparatuses.

A coordinate system 090, in which the direction of static magnetic field is z-direction, and two directions perpendicular to it are x-direction and y-direction, is used. In the following explanations, the same shall apply to all the drawings attached to this specification.

Figure 2:
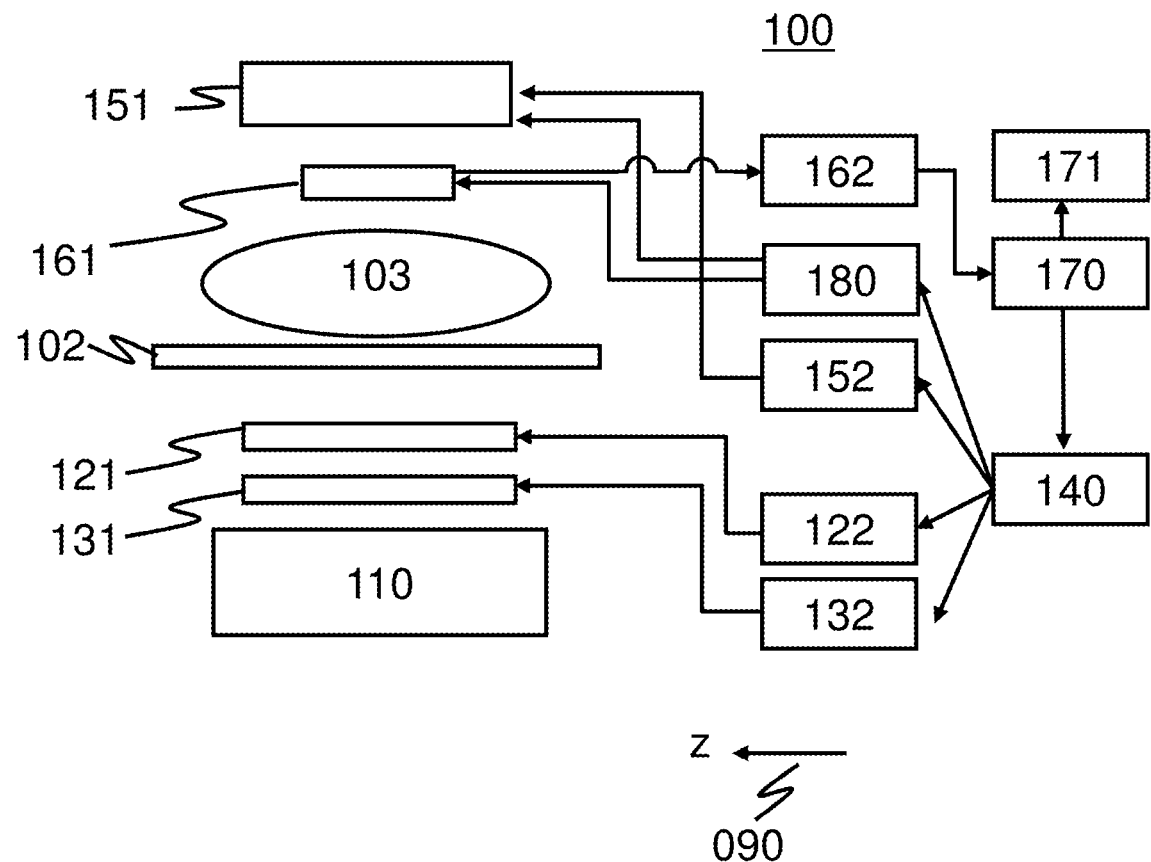
FIG. 2 is a block diagram of an MRI apparatus of the first embodiment.

FIG. 2 is a block diagram showing the schematic configuration of the MRI apparatus 100. As shown in this drawing, the MRI apparatus 100 comprises the horizontal magnetic field type magnet 110, gradient coil 131, transmitting RF coil 151, receiving RF coil 161, gradient magnetic field power supply 132, shim coil 121, shim power supply 122, radio frequency magnetic field generator 152, receiver 162, magnetic coupling-preventing circuit drive 180, computer 170, sequencer 140, and display 171. The apparatus further comprises a table 102 on which a test subject 103 is placed.

The gradient coil 131 is connected to the gradient magnetic field power supply 132, and generates a gradient magnetic field. The shim coil 121 is connected to the shim power supply 122, and adjusts uniformity of the magnetic field. The transmitting RF coil 151 is connected to the radio frequency magnetic field generator 152, and irradiates (transmits) a radio frequency magnetic field on the test subject 103. The receiving RF coil 161 is connected to the receiver 162, and receives a magnetic resonance signal from the test subject 103. The magnetic coupling-preventing circuit drive 180 is connected to a magnetic coupling-preventing circuit (to be explained later). The magnetic coupling-preventing circuit is a circuit for preventing magnetic coupling between the transmitting RF coil 151 and the receiving RF coil 161, which is connected to the transmitting RF coil 151 and the receiving RF coil 161.

The sequencer 140 sends commands to the gradient magnetic field power supply 132, radio frequency magnetic field generator 152, and magnetic coupling-preventing circuit drive 180, and makes them operate. The commands are sent out according to directions from the computer 170. According to the directions from the computer 170, it sets a nuclear magnetic resonance frequency used as a basis for the detection performed by the receiver 162. For example, according to a command from the sequencer 140, a radio frequency magnetic field is irradiated on the test subject 103 by the transmitting RF coil 151. A magnetic resonance signal generated from test subject 103 as a result of the irradiation of the radio frequency magnetic field is detected with the receiving RF coil 161, and detection is performed by the receiver 162.

The computer 170 performs control of the operations of the whole MRI apparatus 100, and various kinds of signal processings. For example, it receives signals detected by the receiver 162 via an A/D conversion circuit, and performs signal processing such as image reconstruction. The results thereof are displayed on the display 171. The detected signals and measurement conditions are stored in a storage medium 132 as required. It also makes the sequencer 140 send commands so that the components operate according to timing and at magnitudes programmed beforehand. When it is necessary to adjust uniformity of the static magnetic field, it makes the sequencer 140 send a command to the shim power supply 122, and thereby makes the shim coil 121 adjust uniformity of the magnetic field.

The magnet 110 constitutes a static magnetic field formation part, which forms the static magnetic field, the gradient coil 131 and the gradient magnetic field power supply 132 constitute a gradient magnetic field formation part, which forms a gradient magnetic field, the radio frequency magnetic field generator 152 constitutes a radio frequency magnetic field generation part, which generates a radio frequency magnetic field, the transmitting RF coil 151 is a transmitting coil, which irradiates the radio frequency magnetic field on the test subject 103, the receiving RF coil 161 is a receiving coil, which detects magnetic resonance signals from the test subject, and the computer 170 constitutes an image reconstruction part, which reconstructs an image from the detected magnetic resonance signals.

[Outline of Transmitting RF Coil and Receiving RF Coil]

Hereafter, the details of the transmitting RF coil 151 and receiving RF coil 161 of this embodiment will be explained. This embodiment will be explained by exemplifying a case where an RF coil having a birdcage shape (birdcage type RF coil) 300 is used as the transmitting RF coil 151, and an array coil 400 comprising adjacently disposed two RF coils having a loop shape (surface coils) is used as the receiving RF coil 161 as an example.

Resonance frequency of the birdcage type RF coil 300 used as the transmitting RF coil 151 is adjusted to the resonance frequency of the element to be excited. In this embodiment, it is adjusted to the magnetic resonance frequency of the hydrogen nucleus, at which hydrogen nucleus can be excited. The array coil 400 used as the receiving RF coil 161 is adjusted so that it can detect magnetic resonance signals of an element that can be excited by the birdcage type RF coil 300.

[Disposition and Connection Scheme of Transmitting RF Coil and Receiving RF Coil]

Figure 3:
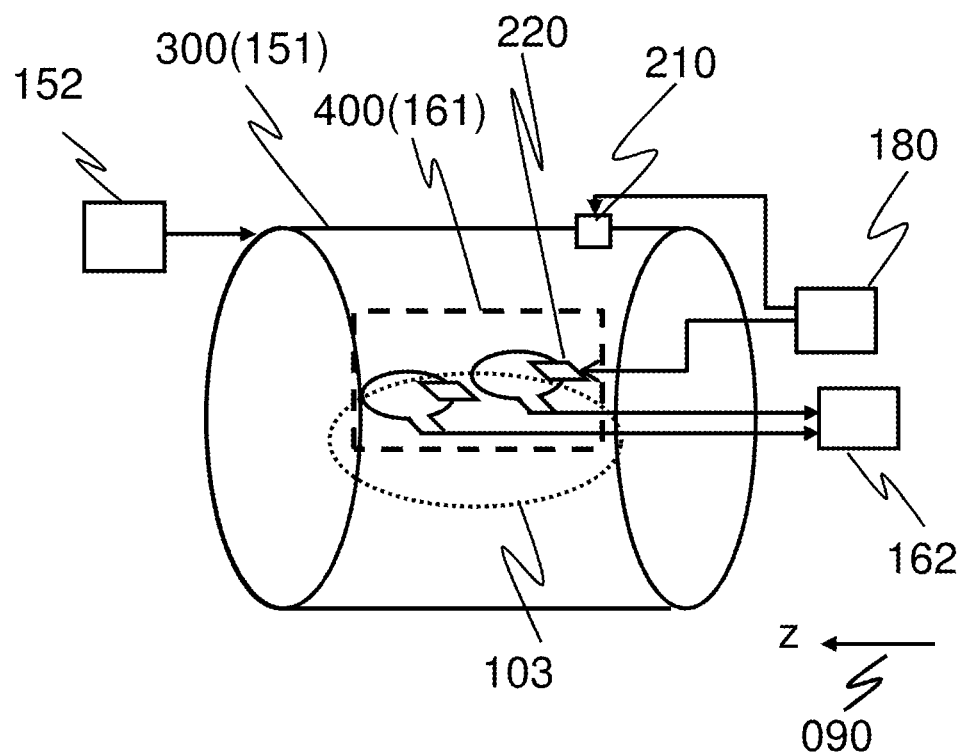
FIG. 3 is an explanatory drawing for explaining connection of transmitting RF coil and receiving RF coil of the first embodiment.

First, disposition of the birdcage type RF coil 300 used as the transmitting RF coil 151, and the array coil 400 used as the receiving RF coil 161, and connection scheme of the birdcage type RF coil 300, array coil 400, radio frequency magnetic field generator 152, receiver 162, and magnetic coupling-preventing circuit drive 180 are explained with reference to FIG. 3.

As shown in this drawing, the birdcage type RF coil 300 and the magnet 110 are coaxially disposed so that the axis of the coil corresponds to the center axis of the magnet. The array coil 400 is disposed in the birdcage type RF coil 300. The birdcage type RF coil 300 is connected to the radio frequency magnetic field generator 152 as described above. The array coil 400 is connected to the receiver 162.

In this embodiment, the birdcage type RF coil 300 further comprises a magnetic coupling-preventing circuit 210, which prevents magnetic coupling with array coil 400. This magnetic coupling-preventing circuit 210 is a circuit that prevents magnetic coupling between the transmitting RF coil 151 (birdcage type RF coil 300) and the receiving RF coil 161 (array coil 400), and is called magnetic coupling between transmitting and receiving coils-preventing circuit 210. This magnetic coupling between transmitting and receiving coils-preventing circuit 210 is inserted into a linear conductor (described later) of the birdcage type RF coil 300 in series.

The array coil 400 comprises a magnetic coupling-preventing circuit 220 that prevents magnetic coupling with the birdcage type RF coil 300. The magnetic coupling-preventing circuit 220 is also a magnetic coupling between transmitting and receiving coils-preventing circuit, which prevents magnetic coupling between the transmitting RF coil 151 (birdcage type RF coil 300) and the receiving RF coil 161 (array coil 400). This magnetic coupling between transmitting and receiving coils-preventing circuit 220 is inserted into each surface coil that constitutes the array coil 400 in series.

The magnetic coupling-preventing circuit drive 180 is connected to these magnetic coupling between transmitting and receiving coils-preventing circuit 210, and magnetic coupling between transmitting and receiving coils-preventing circuit 220.

[Birdcage Type RF Coil]

Figure 4:
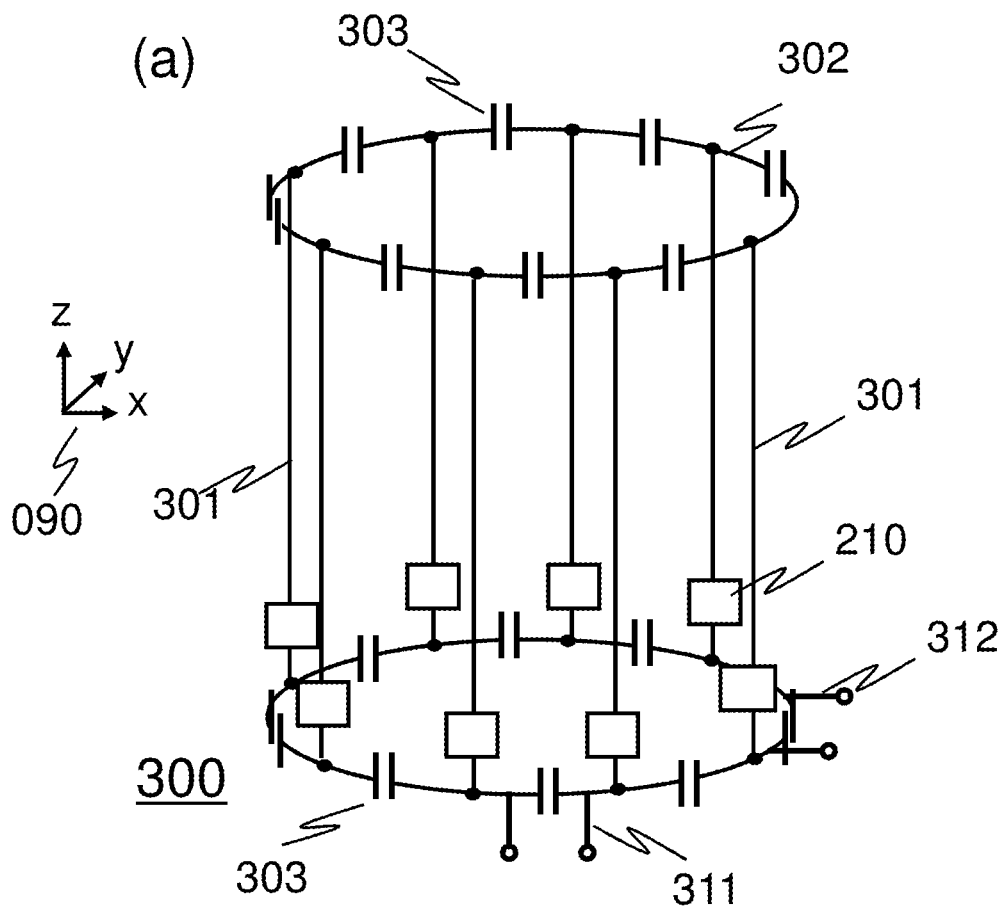
FIG. 4a is an explanatory drawing for explaining configuration of birdcage type RF coil used as the transmitting RF coil of the first embodiment.
FIG. 4b is an explanatory drawing for explaining a circuit for preventing a magnetic coupling between transmission and reception coils (magnetic coupling between transmission and reception coils-preventing circuit) of the first embodiment.
Figure 4:
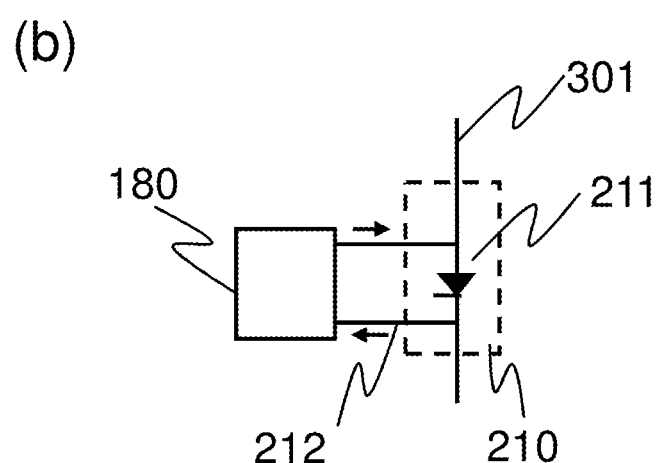
Figure 5:
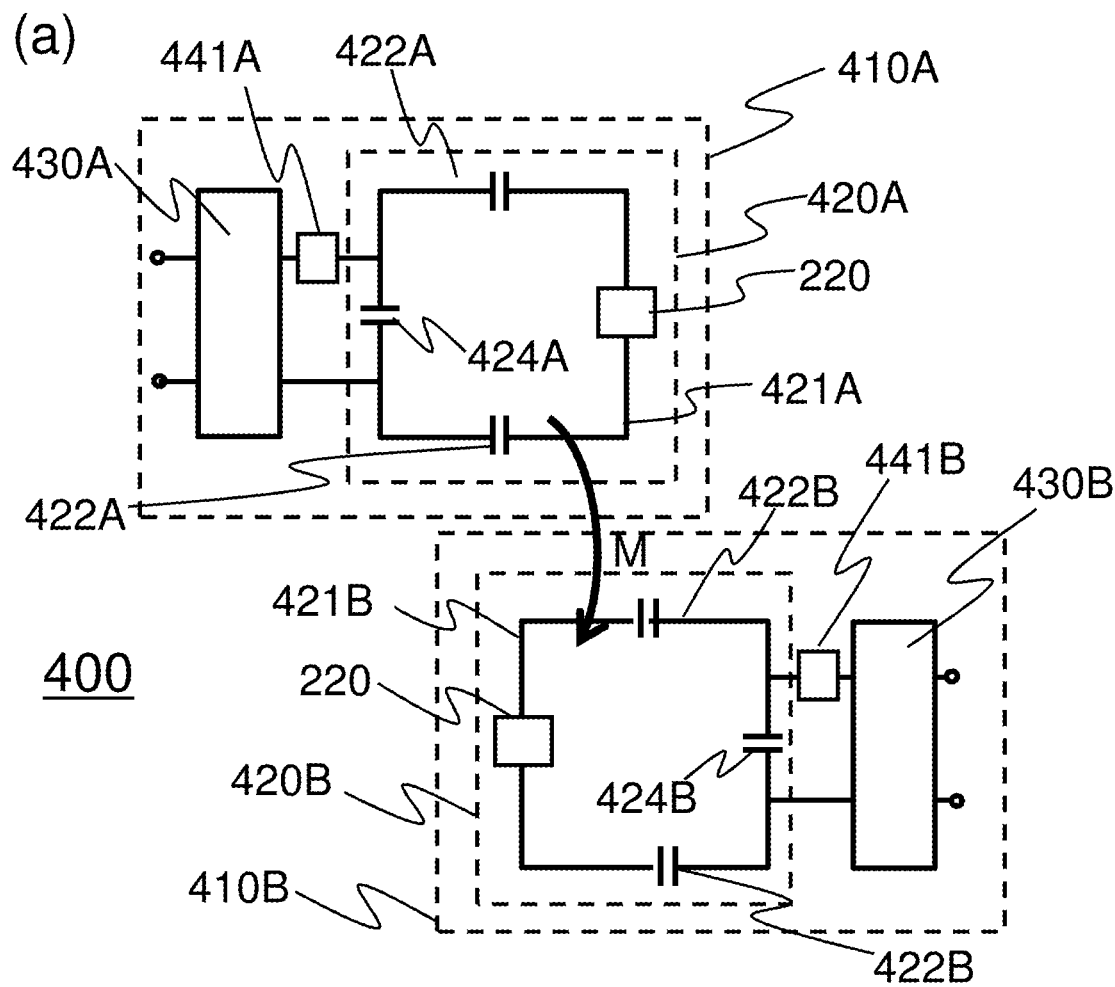
FIG. 5a is an explanatory drawing for explaining configuration of an array coil used as the receiving RF coil of the first embodiment.
FIGS. 5b and 5c are explanatory drawings for explaining the magnetic coupling between transmission and reception coils-preventing circuit of the first embodiment.
Figure 5:
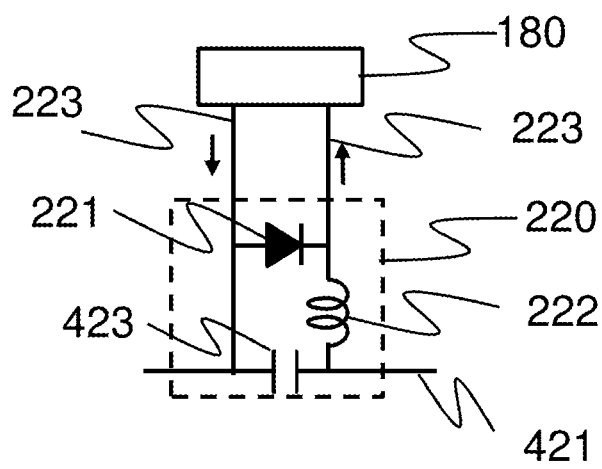
Figure 5:
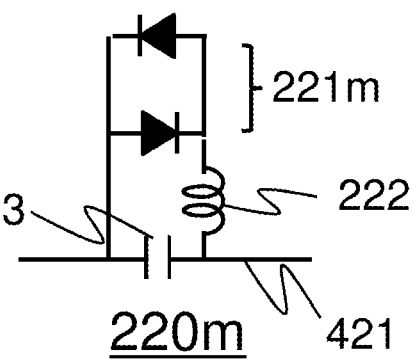
Figure 6:
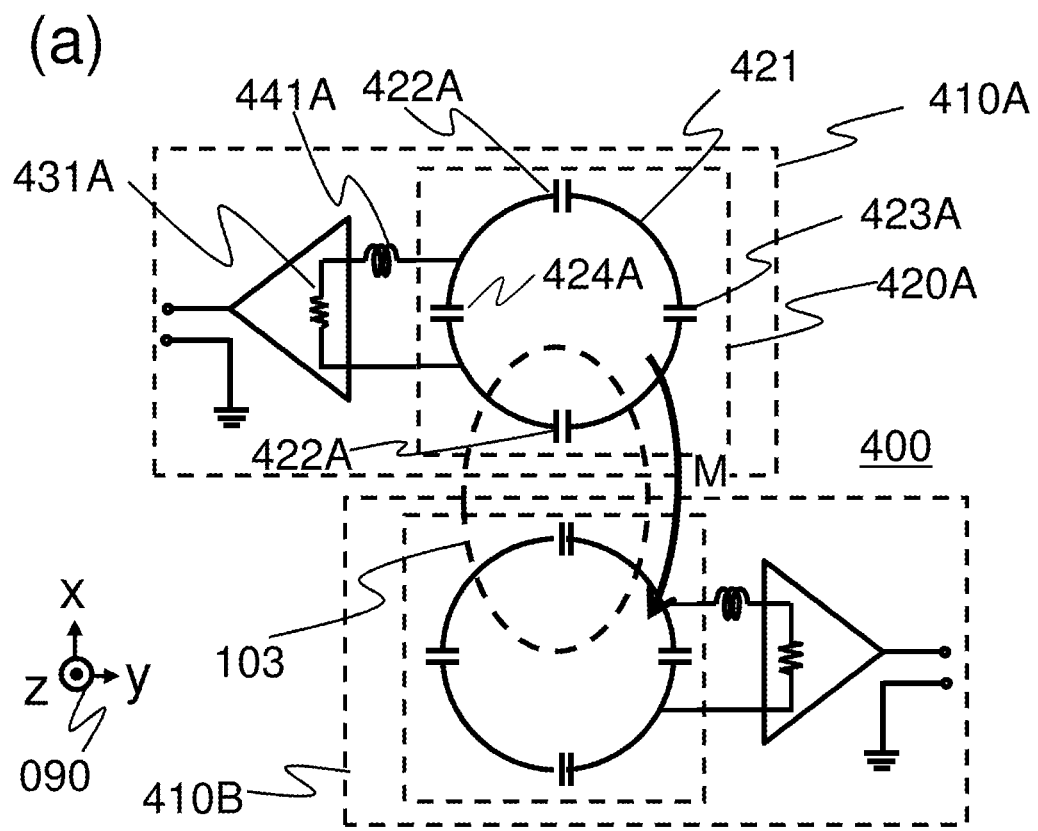
FIGS. 6a and 6b are explanatory drawings for explaining disposition of the array coil of the first embodiment.
Figure 6:
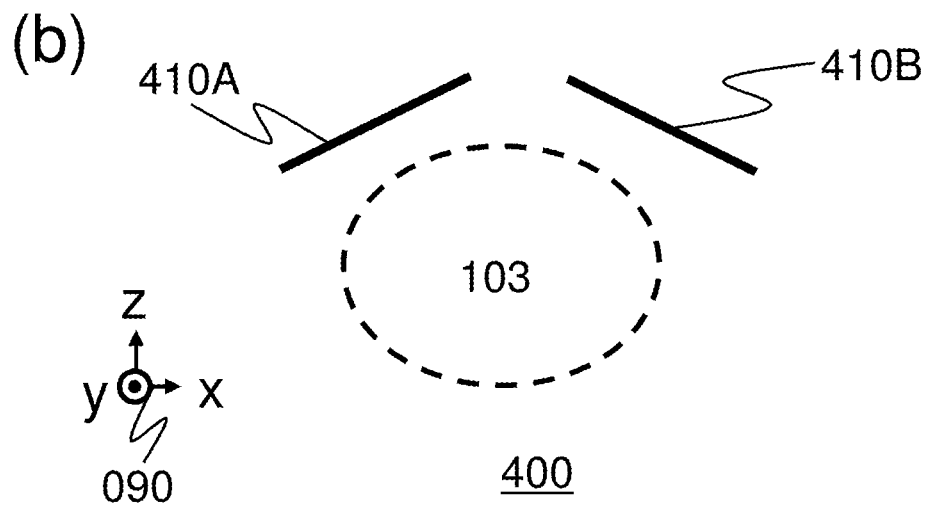
Figure 7:
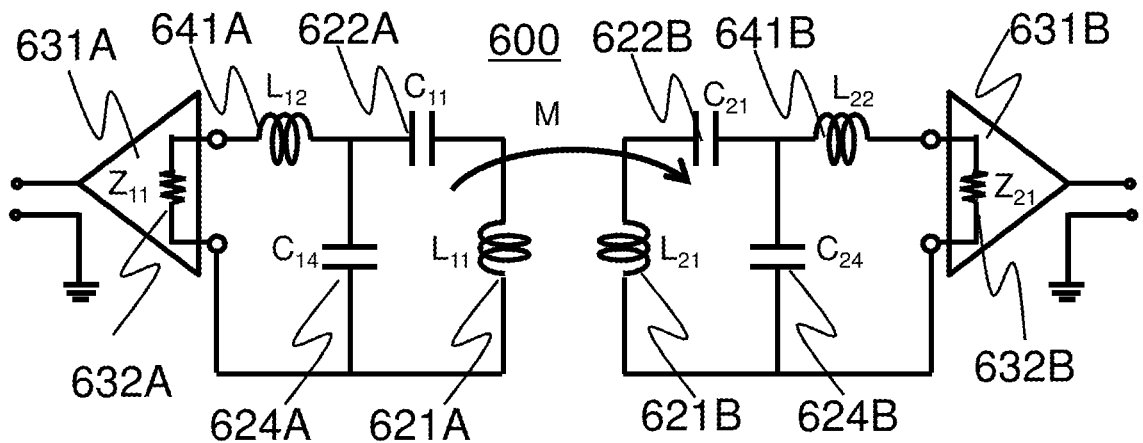
FIGS. 7a to 7c are explanatory drawings for explaining operation of the array coil of the first embodiment.
Figure 7:
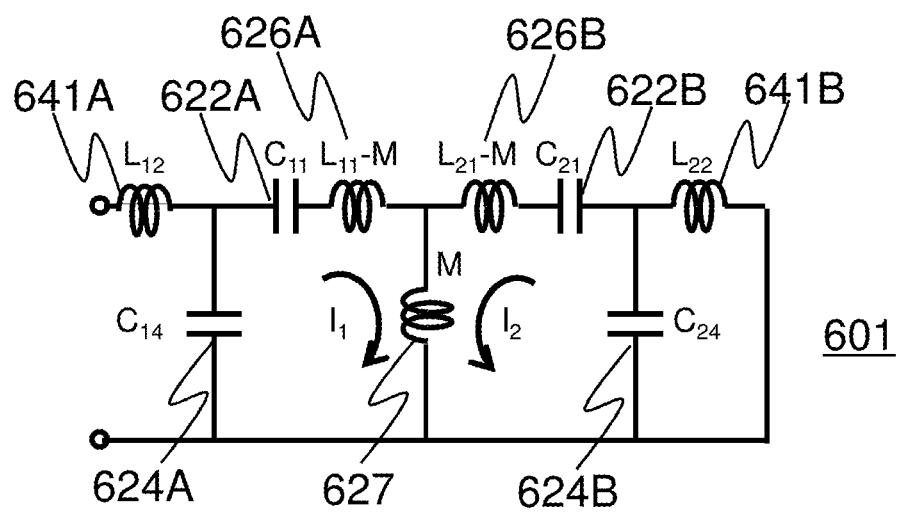
Figure 7:
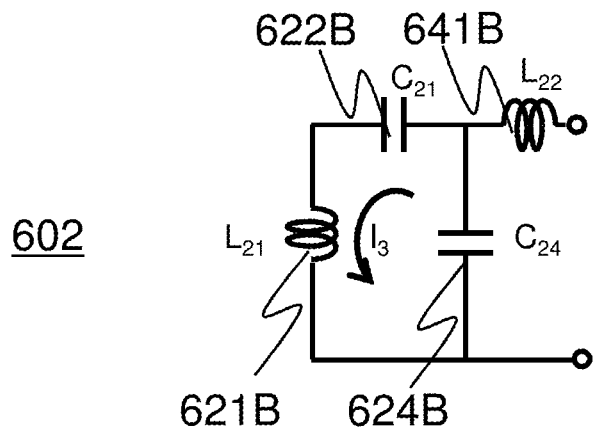

Hereafter, the birdcage type RF coil 300 used as the transmitting RF coil 151 of this embodiment will be explained with reference to FIG. 4. The birdcage type RF coil 300 of this embodiment is adjusted so that the resonance frequency thereof is the resonance frequency of the element to be excited (nuclear magnetic resonance frequency) as described above, and it irradiates a radio frequency magnetic field of that nuclear magnetic resonance frequency. The nuclear magnetic resonance frequency of the radio frequency magnetic field to be irradiated is henceforth represented as $f_0$.

FIG. 4a is a block diagram for explaining the configuration of the birdcage type RF coil 300 of this embodiment. The birdcage type RF coil 300 of this embodiment comprises a plurality of linear conductors 301, end conductors 302 that connects ends of the linear conductors 301, and capacitors 303 inserted into the end conductors 302. The aforementioned magnetic coupling between transmitting and receiving coils-preventing circuit 210 is inserted into each linear conductor 301 in series.

The birdcage type RF coil 300 of this embodiment is provided with two input ports 311 and 312. Transmission signals of which phases differ by 90° are inputted into the first input port 311 and second input port 312, and they are constituted so that a radio frequency magnetic field is efficiently irradiated on the imaging subject (test subject) 103.

[Elimination of Magnetic Coupling Between Transmitting and Receiving Coils]

FIG. 4b is a drawing for explaining the configuration of the magnetic coupling between transmitting and receiving coils-preventing circuit 210 inserted into the linear conductor 301 of the birdcage type RF coil 300, and connection of the same with the magnetic coupling-preventing circuit drive 180. The magnetic coupling between transmitting and receiving coils-preventing circuit 210 comprises a PIN diode 211 and signal wire 212 for control. The PIN diode 211 is inserted into the linear conductor 301 in series, and the signal wire 212 for control is connected to the both ends of the PIN diode 211. The signal wire 212 for control is connected to the magnetic coupling-preventing circuit drive 180. A choking coil is inserted into the signal wire 212 for control in order to avoid mixing of radio frequency signals.

The PIN diode 211 has a characteristic that it is usually highly resistant (OFF state), but when value of direct current that flows through the PIN diode 211 in the forward direction exceeds a certain value, it becomes substantially conductive (ON state). In this embodiment, by using this characteristic, ON and OFF of the PIN diode 211 are controlled on the basis of direct current outputted from the magnetic coupling-preventing circuit drive 180. That is, when a high frequency signal is transmitted, a control current that makes the PIN diode 211 conductive is flown so that the birdcage type RF coil 300 functions as the transmitting RF coil 151. When a magnetic resonance signal is received, a control current is stopped so that the birdcage type RF coil 300 has high impedance to attain open state.

As described above, in this embodiment, by controlling the direct current (control current) flown from the magnetic coupling-preventing circuit drive 180, the birdcage type RF coil 300 is operated as the transmitting RF coil 151 at the time of radio frequency signal transmission, and it is made to be in an open state at the time of magnetic resonance signal reception to eliminate magnetic coupling with the array coil 400 as the receiving RF coil 161.

[Array Coil]

Hereafter, the array coil 400 used as the receiving RF coil 161 of this embodiment will be explained with reference to FIGS. 5a to 7c. As described above, the array coil 400 of this embodiment comprises two subcoils 410. Each of the two subcoils can receive magnetic resonance signals, and functions as one channel.

FIG. 5a is a block diagram for explaining the configuration of the array coil 400 of this embodiment. Two of the subcoils 410 that constitute the array coil 400 of this embodiment are called first subcoil 410A and second subcoil 410B, respectively. The first subcoil 410A and second subcoil 410B are surface coils having a loop formed in a plane. The first subcoil 410A and second subcoil 410B each receive a magnetic resonance signal. The received signal is sent to the receiver 162.

In the following explanations, when it is not particularly necessary to distinguish constituent components of the respective subcoils 410 constituting the array coil 400 for the respective subcoils 410, the alphabets to be attached to the numerals for referring to them are omitted.

The first subcoil 410A comprises a loop coil part 420 (first loop coil part 420A) that receives a magnetic resonance signal, low (input) impedance signal processing circuit 430 (first low impedance signal processing circuit 430A), and magnetic coupling-adjusting part 441 (first magnetic coupling-adjusting part 441A) that connects the loop coil part 420 and low impedance signal processing circuit 430. The magnetic coupling-adjusting part 441 is constituted by at least either one of a capacitor and inductor.

The loop portion (first loop 421A) of the first loop coil part 420A is formed with a conductor. The first loop coil part 420A comprises a capacitor 424A inserted in series with respect to inductor component of the first loop 421A. This inductor component and the capacitor 424A constitute a parallel resonant circuit. In order to distinguish this capacitor 424A from the other capacitors, it is referred to as first parallel capacitor 424A.

A capacitor 422A that adjusts resonance frequency, and the magnetic coupling between transmitting and receiving coils-preventing circuit 220 are inserted into the first loop 421A in series. In order to distinguish this capacitor 422A from the other capacitors, it is referred to as first series capacitor 422A. Although the loop comprising two of the first series capacitors 422A is exemplified here, the number of the first series capacitor 422A may be one or larger.

As described above, the first subcoil 410A of this embodiment comprises, as circuit elements for adjustment, the first magnetic coupling-adjusting part 441A, first series capacitor 422A serially inserted with respect to the inductor component of the first loop 421A, and first parallel capacitor 424A that is serially inserted with respect to the inductor component and makes the first loop coil part 420A to be a parallel resonant circuit.

One terminal of the low impedance signal processing circuit 430 on the side of the loop coil part 420 is connected to one end of the parallel capacitor 424 of the loop coil part 420 via the magnetic coupling-adjusting part 441. Another terminal of the low impedance signal processing circuit 430 on the side of the loop coil part 420 is directly connected to the other end of the parallel capacitor 424 of the loop coil part 420. The other terminal of the low impedance signal processing circuit 430 not on the side of the loop coil part 420 is connected to the receiver 162.

The magnetic coupling between transmitting and receiving coils-preventing circuit 220 eliminates magnetic coupling with the birdcage type RF coil 300 as the transmitting RF coil 151.

The second subcoil 410B also has the same configuration as that of the first subcoil 410A. That is, the second subcoil 410B comprises a second loop coil part 420B as a parallel resonant circuit, second low impedance signal processing circuit 430B, second magnetic coupling-adjusting part 441B that connects the second loop coil part 420B and the second low impedance signal processing circuit 430B. The second loop coil part 420B comprises a loop formed with a conductor (second loop 421B), second series capacitor 422B serially inserted with respect to inductor component of the second loop 421B, and second parallel capacitor 424B that is serially inserted with respect to the inductor component and makes the second loop coil part 420B to be a parallel resonant circuit.

[Elimination of Magnetic Coupling Between Transmitting and Receiving Coils]

Elimination of magnetic coupling between the transmitting RF coil 151 (birdcage type RF coil 300) and receiving RF coil 161 (array coil 400) by the magnetic coupling between transmitting and receiving coils-preventing circuit 220 will be explained. FIG. 5b is a drawing for explaining the configuration of the magnetic coupling between transmitting and receiving coils-preventing circuit 220 inserted into the loop 421, and connection between the magnetic coupling between transmitting and receiving coils-preventing, circuit 220 and the magnetic coupling-preventing circuit drive 180.

The magnetic coupling between transmitting and receiving coils-preventing circuit 220 comprises a PIN diode 221, inductor 222, and signal wire 223 for control.

The PIN diode 221 and the inductor 222 are serially connected, and connected to the capacitor 423 in parallel. The capacitor 423 is a capacitor inserted into the loop 421. The signal wire 223 for control is connected to the both ends of the PIN diode 221. The signal wire 223 for control is connected to the magnetic coupling-preventing circuit drive 180. A choking coil (not shown in the drawing) is inserted into the signal wire 223 for control in order to avoid mixing of radio frequency signals. The inductor 222 and the capacitor 423 are adjusted so that they resonate in parallel at the frequency of the received magnetic resonance signal.

The parallel resonant circuit has a characteristic that it generally shows high impedance (high resistance) at a resonance frequency. Therefore, if an electric current flows in the PIN diode 221, the PIN diode 221 is turned on, the capacitor 423 of the loop 421 resonates in parallel with the inductor 222 at the frequency of the received magnetic resonance signal, and comes to show high impedance. Therefore, a part of the loop coil part 420 shows high impedance and the loop coil part 420 becomes to be opened at the frequency of the received magnetic resonance signal, and the subcoil 410 having the loop coil part 420 is also opened.

As described above, when an electric current flows through the PIN diode 221, and it comes to be in an ON state, magnetic coupling between the subcoils 410A and 410B and the birdcage type RF coil 300 is thereby eliminated. Therefore, magnetic coupling of the array coil 400 comprising the subcoils 410 as coil elements and the birdcage type RF coil 300 is also eliminated.

Number of the magnetic coupling between transmitting and receiving coils-preventing circuit 220 inserted into the subcoil 410 is not limited to the number mentioned above. Two or more of the circuits may be inserted into each loop 421. Magnetic coupling can sufficiently be reduced by inserting a plurality of the circuits.

The configuration of the magnetic coupling between transmitting and receiving coils-preventing circuit 220 is not also limited to the aforementioned configuration. For example, as a modification of the magnetic coupling between transmitting and receiving coils-preventing circuit 220m shown in FIG. 5c, a cross diode 221m may be used instead of the PIN diode 221. With such a configuration, when an intense signal flows through the conductor constituting the loop 421, the cross diode 221m is turned on, and the capacitor 423 of the loop 421 resonates in parallel with the inductor 222 at the frequency of the received magnetic resonance signal, and comes to show high impedance. In this case, it is not necessary to provide the magnetic coupling-preventing circuit drive 180.

[Disposition and Control of Individual Subcoils]

In the array coil 400 of this embodiment, the first subcoil 410A and the second subcoil 410B are adjusted so that each can receive a magnetic resonance signal. The first subcoil 410A is adjusted so that the resonance frequency of the first subcoil 410A alone differs from the nuclear magnetic resonance frequency, which is the frequency of the magnetic resonance signal as the object of transmission and reception. By disposing the first subcoil 410A at such a position or in such a configuration that it can magnetically couple with the second subcoil 410B to intentionally cause magnetic coupling, the first subcoil 4110A is adjusted so that a circling electric current path is formed in each of the first loop 421A and the second loop 421B, and it resonates at the nuclear magnetic resonance frequency. Specifically, the first subcoil 410A is disposed at such a position that the resonance frequency characteristic of the subcoil 410A changes depending on the presence or absence of the second subcoil 410B, and adjusted.

[Disposition]

In the array coil 400, the first subcoil 410A and the second subcoil 410B are disposed at such positions that they can magnetically couple with each other. That is, they are disposed at such positions that the loop coil part 420A of the first subcoil 410A and the loop coil part 420B of the second subcoil 410B are disposed in substantially the same plane, and magnetic fields formed by the first subcoil 410A and the second subcoil 410B can mutually interfere. The first subcoil 410A and the second subcoil 410B may be disposed so that the coil elements thereof partially overlap with each other, so long as they are disposed so that they magnetically couple with each other.

A specific example of such disposition is explained with reference to FIGS. 6a and 6b. FIGS. 6a and 6b are drawings for explaining disposition of the first subcoil 410A and the second subcoil 410B, which constitute the array coil 400 used as the receiving RF coil 161 of this embodiment.

In FIG. 6a, the vertical direction is referred to as X-axis direction, the horizontal direction as Y-axis direction, and the direction perpendicular to the drawing as Z-axis direction, as shown in the coordinate system 090. In FIG. 6b, the vertical direction is referred to as Z-axis direction, the horizontal direction as X-axis direction, and the direction perpendicular to the drawing as Y-axis direction, as shown in the coordinate system 090.

Hereafter, this embodiment will be explained by exemplifying a case in which, as shown in FIGS. 6a and 6b, the first subcoil 410A and the second subcoil 410B are disposed so that the faces of the loops 421 of the loop coil parts 420 are relatively close to a plane which is approximately perpendicular to the direction of the magnetic field (Z-axis direction), as an example. The loop 421 of the loop coil part 420 has a circular shape.

For example, the diameters of the loops 421A and 421B of the first loop coil part 420A and the second loop coil part 420B shall be 100 mm. In this case, as distances and positions for causing magnetic coupling, the first subcoil 410A is disposed in a plane corresponding to the XY plane rotated counterclockwise by 20° around the Y axis as the rotation axis, and the second subcoil 410B is disposed in a plane corresponding to the XY plane rotated clockwise by 20° around the Y axis as the rotation axis. The distance between the origin points of the circles of the circular loops 421 of the two subcoils 410 shall be 132 mm.

Magnitude M of mutual inductance between two of the subcoils 410A, 410B disposed in such a positional relationship that magnetic coupling is caused between them is represented by the following equation (1).

[Equation 1]

$$M = k\sqrt{L_{11} L_{21}}) \quad (1)$$

In the equation, k is the magnetic coupling coefficient, which is a value representing a ratio of magnetic flux coupling with the subcoil 410B to the total magnetic flux formed by the subcoil 410A. The magnetic coupling coefficient k takes a value of from 0 to 1. $L_{11}$ is magnitude of the inductor component of the loop 421A of the first subcoil 410A. $L_{21}$ is magnitude of the inductor component of the loop 421B of the second subcoil 410B.

In FIG. 6a, there is exemplified a case where low input impedance signal amplifiers 431A and 431B are used as the first low impedance signal processing circuit 430A and the second low impedance signal processing circuit 430B.

Use of the low input impedance signal amplifier 431 as the low impedance signal processing circuit 430 enables immediate amplification of a signal detected by the loop coil part 420, and therefore enables acquisition of data containing few noises. As the low input impedance signal amplifier 431, one for input impedance of 2Ω was used. The low impedance signal processing circuit 430 is not limited to the low input impedance signal amplifier 431.

[Adjustment of Circuit Elements]

Hereafter, adjustment of circuit elements of the array coil 400 will be explained. The following explanations will be focused mainly on the operation at the time of reception. In this embodiment, magnetic coupling between the transmitting RF coil 151 and the receiving coil 161 is eliminated by the aforementioned procedure using the magnetic coupling between transmitting and receiving coils-preventing circuits 210 and 220. In this section, it is supposed that the transmitting RF coil 151 is always opened, and explanation on elimination of magnetic coupling between the transmitting RF coil 151 and receiving RF coil 161 is omitted.

The first subcoil 410A and the second subcoil 410B of the array coil 400 of this embodiment realize the aforementioned functions through adjustment of values of the first magnetic coupling-adjusting part 441A, second magnetic coupling-adjusting part 441B, first series capacitors 422A and 423A, second series capacitors 422B and 423B, first parallel capacitor 424A, and second parallel capacitor 424B.

Adjustment of these circuit elements will be explained with reference to an equivalent circuit of the array coil 400.

FIG. 7a shows an equivalent circuit 600 of the array coil 400 of this embodiment. In this drawing, value $L_{11}$ of the inductor 621A is the inductor component of the first loop 421A, and value $C_{11}$ of the series capacitor 622A is a synthesized value of those of the series capacitors (422A, 423A) inserted into the first loop 421A. Similarly, value $L_{21}$ of the inductor 621B is the inductor component of the second loop 421B, and value $C_{21}$ of the series capacitor 622B is a synthesized value of those of the series capacitors (422B, 423B) inserted into the second loop 421B.

Value $C_{14}$ of the parallel capacitor 624A is the value of the parallel capacitor 424A, and value $C_{24}$ of the parallel capacitor 624B is the value of the parallel capacitor 424B.

An inductor is used for the magnetic coupling-adjusting part 441. Value $L_{12}$ of the inductor 641A is the value of the inductor of the first magnetic coupling-adjusting part 441A. Value $L_{22}$ of the inductor 641B is the value of the inductor of the second magnetic coupling-adjusting part 441B. In the explanation of this embodiment, an inductor is used for the magnetic coupling-adjusting part 441, but this embodiment is not limited to this configuration. The parallel capacitor 624 and the magnetic coupling-adjusting part 441 are usually connected with a conductor. Since the conductor also has an inductor component, a parallel resonant circuit is formed by the parallel capacitor 624, magnetic coupling-adjusting part 441, and inductor component of the conductor connecting them, even if an inductor is not further added. So long as the resonance frequency of this parallel resonant circuit can be adjust with a certain means, the magnetic coupling-adjusting part 441 may be a capacitor, or a parallel circuit of a capacitor and an inductor. In the following explanations, it is supposed that the conductor connecting the parallel capacitor 624 and the magnetic coupling-adjusting part 441 does not have inductor component for simplicity of the explanations.

Value $Z_{11}$ of the impedance 632A is the value of the input impedance of the low input impedance signal amplifier 431A used as the first low impedance signal processing circuit 430A. Value $Z_{21}$ of the impedance 632B is the value of the input impedance of the low input impedance signal amplifier 431B used as the second low impedance signal processing circuit 430B. Since these impedances $Z_{11}$ and $Z_{21}$ are sufficiently low impedances, they are henceforth regarded to be 0Ω (short circuit).

The mutual inductance M is the value of the mutual inductance of the first loop coil part 420A (620A) and the second loop coil part 420B (620B).

Frequency of the magnetic resonance signal to be detected (nuclear magnetic resonance frequency) is represented as $f_0$. Resonance frequency of the first subcoil 410A (610A) alone is represented as $f_{10}$, and resonance frequency of the second subcoil 410B (610B) alone is represented as $f_{20}$. Resonance frequencies of the first loop coil part 420A (620A) and the second loop coil part 420B (620B), which are parallel resonant circuits, are represented as $f_{12}$ and $f_{22}$, respectively. As for the disposition shown in FIGS. 6a and 6b, resonance frequency of the first subcoil 410A (610A) except for the first low impedance signal processing circuit 430A (631A) (henceforth referred to as first resonance part) relative to the first low impedance signal processing circuit 430A (631A) at the time of signal reception is represented as $f_{11}$, and resonance frequency of the second subcoil 410B (610B) except for the second low impedance signal processing circuit 430B (631B)(henceforth referred to as second resonance part) relative to the second low impedance signal processing circuit 430B (631B) at the time of signal reception is represented as $f_{21}$.

The values of the circuit elements of the array coil 400 of this embodiment are adjusted so that the following equations (2) to (5) are satisfied.

$$f_{11} = f_{22} = f_{20} = f_0 \quad (2)$$

$$f_{10} \neq f_0 \quad (3)$$

[Equation 4]

$$\frac{1}{2\pi\sqrt{L_{22} C_{24}}} \neq f_0 \quad (4)$$

-continued $$\frac{1}{2\pi\sqrt{L_{12}C_{14}}} = f_0 \quad (5)$$

If the values of the circuit elements are adjusted according to the equation (4), the resonance frequency of the parallel resonant circuit constituted by the adjustment inductor 441B (641B) and the parallel capacitor 424B (624B) of the second subcoil 410B (610B) (henceforth referred to as $L_{22}C_{24}$ resonant circuit) should differ from the nuclear magnetic resonance frequency $f_0$. Therefore, at the time of signal reception, resistance does not become high between the both ends of the capacitor 424B of the second subcoil 410B, and the second subcoil 410B magnetically couples with the first subcoil 410A.

An equivalent circuit 601 of the first subcoil 410A except for the first low impedance signal processing circuit 430A (631A) (first resonance part) relative to the first low impedance signal processing circuit 430A (631A) in a state that the first loop coil part 420A and the second loop coil part 420B are magnetically coupled by the aforementioned adjustment is shown in FIG. 7b.

That is, at the time of signal reception, the first resonance part of the first subcoil 410A serves as the circuit 601 in which the inductor component ($L_{11}$) of the first loop 421A and the inductor component ($L_{21}$) of the second loop 421B are coupled by magnetic coupling, as shown in FIG. 7b.

In this drawing, the inductor 627 shows a mutual inductance M, and the value $L_{11}$-M of the inductor 626A, and the value $L_{21}$-M of the inductor 626B are obtained by subtracting the mutual inductance M from the inductor components of the loops 421, respectively.

In this configuration, if the values of the circuit elements are adjusted so that a circling electric current flows clockwise in the first loop 421A, and a circling electric current $I_2$ flows counterclockwise in the second loop 421B as shown in FIG. 7b, an electric current path like that of a butterfly coil is effectually formed by the loop 421A and loop 421B, and an electric current flows in it (FIG. 7b).

If the values of the circuit elements are adjusted so that a circling electric current flows clockwise in both the first loop 421A and the second loop 421B, an electric current path like that of one loop coil formed by two of loop coils, the first loop 421A and second loop 421B, is formed, and an electric current flows in it (not shown in the drawing).

If the values of the circuit elements are adjusted according to the equation (5), the resonance frequency of the parallel resonant circuit constituted by the adjustment inductor 441A (641A) and the parallel capacitor 424A (624A) of the first subcoil 410A (610A) (henceforth referred to as $L_{12}C_{14}$ resonant circuit) should become the nuclear magnetic resonance frequency $f_0$. Therefore, at the time of signal reception, resistance becomes high between the both ends of the capacitor 424A of the first subcoil 410A. Therefore, the second subcoil 410B does not magnetically couple with the first subcoil 410A.

An equivalent circuit 602 of the second subcoil 410B except for the second low impedance signal processing circuit 430B (631B) (first resonance part) relative to the second low impedance signal processing circuit 430B (631B) in a state that the adjustment is performed according to the equation (5) is shown in FIG. 7c.

The first subcoil 410A is adjusted so that magnetic coupling thereof with the first subcoil 410B is prevented at the time of signal reception. Therefore, at the time of signal reception, the resonance part of the second subcoil 410B becomes the same circuit 602 as that of the second subcoil 410B alone, as shown in FIG. 7c.

If the values of the circuit elements are adjusted according to the equation (3), the resonance frequency $f_{10}$ of the first subcoil 410A alone shall differ from the nuclear magnetic resonance frequency $f_0$.

Further, if the values of the circuit elements are adjusted according to the equation (2), the resonance frequency $f_{20}$ of the second subcoil 410B alone, resonance frequency $f_{11}$ of the first resonance part, and resonance frequency $f_{22}$ of the second loop coil part 420B at the time of signal reception become equal to the nuclear magnetic resonance frequency $f_0$. The second subcoil 410B is thereby comes to be able to detect a magnetic resonance signal by itself. Further, the first subcoil 410A magnetically couples with the second subcoil 410B at the time of signal reception as described above. At this time, the resonance frequency of the first resonance part becomes equal to the nuclear magnetic resonance frequency $f_0$. Therefore, the subcoil 410A also comes to be able to detect a magnetic resonance signal in a magnetically coupled state.

The adjustment is performed by adjusting the values of the series capacitor 622, parallel capacitor 624, and adjustment inductor 641 as described above. In this embodiment, since the value of the inductor 621 of the loop 421 is determined by the shape of the loop 421, it cannot be changed. The value M of the mutual inductance is determined by shape and disposition relationship.

By performing the adjustment as described above, each of the subcoils 410 comes to be able to receive a magnetic resonance signal as the detection object.

At the time of signal reception, the first subcoil 410 magnetically couples with the second subcoil 410 as shown in FIG. 7b, and functions as a subcoil showing a large and deep sensitivity area. Further, by adjusting the value of the capacitor or inductor of the magnetic coupling-adjusting part 441, magnitude of magnetic coupling can be changed, and sensitivity profile can be thereby adjusted.

On the other hand, the second subcoil 410 does not magnetically couple with the first subcoil 410, but it functions as an independent subcoil as shown in FIG. 7c. Therefore, the first subcoil 410A and the second subcoil 410B show different sensitivity profiles with respect to an imaging region at the time of signal reception. Therefore, they function as a multi-channel coil.

[Example of Adjustment]

Hereafter, the adjustment procedure for the circuit elements of this embodiment will be explained with reference to a specific example. The following explanation is made by exemplifying a case where the array coil 400 is adjusted so that it resonates at the magnetic resonance frequency of the atomic nucleus of hydrogen, 124 MHz ($f_0$=124 MHz). As shown in FIG. 7b, in this example, the adjustment is performed so that an electric current flows clockwise in the loop 421A and an electric current flows counterclockwise in the second loop 421B, thus an electric current path like that of a butterfly coil is effectually formed by the loop 421A and the loop first 421B when the first subcoil 410A magnetically couples with the second subcoil 410B. Specifically, for the disposition of the loop 421A and loop 421B of this embodiment, the adjustment is performed so that the resonance frequency of the parallel resonant circuit constituted by the inductor 641B and the parallel capacitor 624B ($L_{22}C_{24}$ resonant circuit) becomes smaller than $f_0$.

First, the circuit elements of the second subcoil 410B are adjusted. At the time of this adjustment, the loop coil part 420A of the first subcoil 410A is opened.

Values of capacity $C_{21}$ of the series capacitor 622B and capacity $C_{24}$ of the parallel capacitor 624B are adjusted. In this adjustment, these values are adjusted so that the equivalent circuit 602 shown in FIG. 7c resonates at 124 MHz, and impedance between the both ends of the series circuit of the inductor 641B and parallel capacitor 624B becomes 50Ω.

At the same time, value $L_{22}$ of the inductor 641B and value $C_{24}$ of the parallel capacitor 624B are adjusted so that the equation (4) is satisfied.

In this adjustment, the values of $L_{22}$ and $C_{24}$ are determined so that the parallel resonant circuit formed by the adjustment inductor 641B and the parallel capacitor 624B functions as a capacitor, and thereby an electric current flows as described above at the time of coupling. This adjustment is performed on the basis of the characteristic principle of parallel resonant circuit. The characteristic principle of parallel resonant circuit will be explained later. Specifically, these values are adjusted so that the resonance frequency of the parallel resonant circuit constituted by the inductor 641B and the parallel capacitor 624B ($L_{22}C_{24}$ resonant circuit) becomes smaller than $f_0$. The value smaller than $f_0$ is, for example, 90 MHz.

Then, values of the circuit elements of the first subcoil 410A are adjusted. For this adjustment, it is supposed that the circuit elements of the second subcoil 410B shall have been adjusted as described above.

In this adjustment, value $C_{11}$ of the series capacitor 622A and value $C_{14}$ of the parallel capacitor 624A are adjusted so that the equivalent circuit 601 shown in FIG. 7b resonates at 124 MHz, and the impedance between the both ends of the series circuit of the inductor 641A and the parallel capacitor 624A ($C_{14}$) becomes 50Ω.

At the same time, in order that the second subcoil 410B should not magnetically couple with the first subcoil 410A, value $L_{12}$ of the adjustment inductor 641A and value $C_{14}$ of the parallel capacitor 624A are adjusted so that the equation (5) is simultaneously satisfied. As a result, the first subcoil 410A can be regarded as a circuit in which high impedance is inserted into the first loop 421A, with regard to the second subcoil 410B. Therefore, the second subcoil 410B does not magnetically couple with the first subcoil 410A.

The adjustment of these first subcoil 410A and second subcoil 410B may be repeated several times as required.

When the value smaller than $f_0$ is 90 MHz, values of the parameters adjusted by the aforementioned adjustments are, for example, $C_{11}$=7.7 pF, $C_{14}$=148 pF, $C_{21}$=98 pF, $C_{24}$=7.9 pF, $L_{12}$=11 nH, and $L_{22}$=26 nH.

As a result of the adjustments described above, the array coil 400 of this embodiment resonates at the nuclear magnetic resonance frequency, and receives a magnetic resonance signal. The magnetic coupling of two of the subcoils 410A and 410B effectually increases the size of the coil, and expands the sensitivity area. Further, current distribution like that of a butterfly coil or large surface coil is constituted, sensitivity profile that cannot be obtained only with two small surface coils is constituted, and thereby signals are efficiently (highly sensitively) obtained. That is, even for regions for which it has been difficult to increase sensitivity because of the relationship between the direction of the static magnetic field and the magnetic field of the RF coil, such as parietal region of imaging subject in the case of tunnel type MRI (MRI apparatus 100 of the horizontal magnetic field type), and front abdominal surface in the case of open type MRI (MRI apparatus 101 of the vertical magnetic field type), sensitivity can be increased by using this embodiment.

[Characteristic Principle of Parallel Resonant Circuit]

Figure 8:
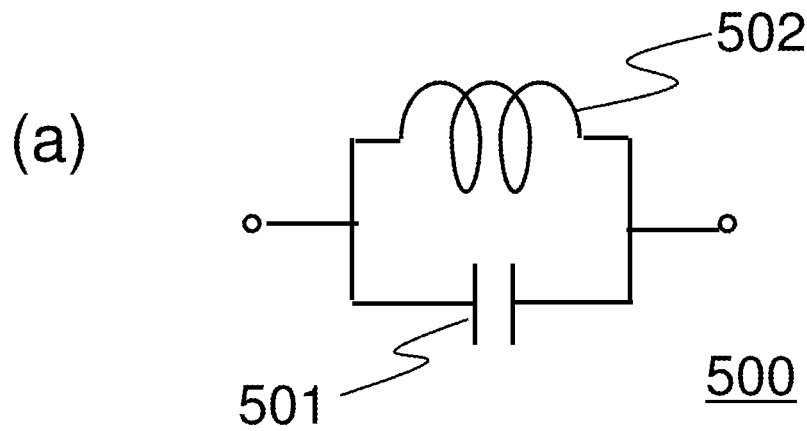
FIGS. 8a and 8b are explanatory drawings for explaining operation of a conventional parallel resonant circuit.
Figure 8:
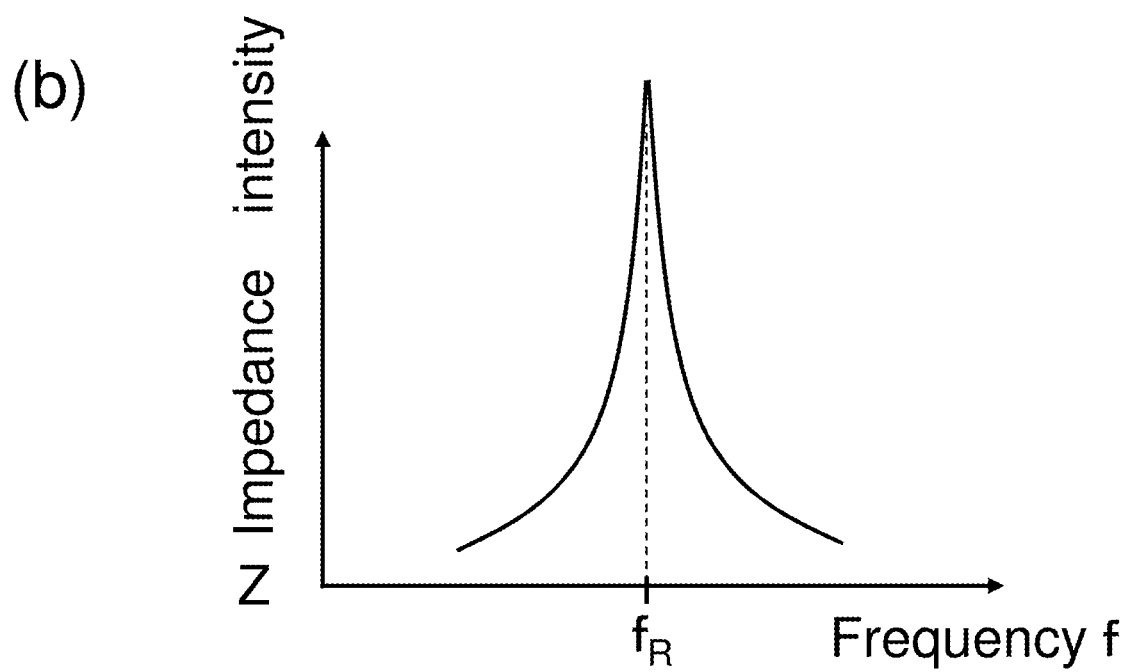

Hereafter, operation of a general parallel resonant circuit will be explained. FIGS. 8a and 8b are drawings for explaining operation of a parallel resonant circuit.

As a parallel resonant circuit 500, an inductor 502 (L) and a capacitor 501 (C) are connected in parallel as shown in FIG. 8a. Impedance Z between the both ends of the parallel resonant circuit 500 is represented by the following equation (6), wherein f represents frequency of voltage applied to the parallel resonant circuit 500, and ω represents angular frequency (ω=2πf).

[Equation 6]

$$\frac{1}{Z} = j\omega C + \frac{1}{j\omega L} \quad (6)$$

The impedance Z changes depending on the applied frequency f as shown in FIG. 8b, and resonance occurs when the frequency f is $f_R$. That is, the impedance Z between the both ends of the parallel resonant circuit 500 becomes the maximum at the frequency $f_R$.

For a frequency lower than the resonance frequency $f_R$ of the parallel resonant circuit 500 (f<$f_R$), the impedance Z is represented by the equation (7), and the parallel resonant circuit 500 operates as an inductive reactance (inductor).

[Equation 7]

$$Z = \frac{1 - (f/f_R)^2}{J2\pi f L} \quad (7)$$

Value L' of apparent inductance of the parallel resonant circuit 500 is represented by the equation (8).

[Equation 8]

$$L' = \frac{L}{1 - (f/f_R)^2} \quad (8)$$

On the other hand, at a frequency higher than the resonance frequency $f_R$ of the parallel resonant circuit 500 (f>$f_R$), the impedance Z is represented by the equation (9), and the parallel resonant circuit 500 operates as a capacitive reactance (capacitor).

[Equation 9]

$$Z = J2\pi f C \frac{(f/f_R)^2 - 1}{(f/f_R)^2} \quad (9)$$

Value C' of apparent capacitance of the parallel resonant circuit 500 is represented by the equation (10).

[Equation 10]

$$C' = \frac{(f/f_R)^2 - 1}{(f/f_R)^2} C \quad (10)$$

As described above, the parallel resonant circuit 500 operates in different manners depending on the resonance frequency f of applied voltage, and $f_R$ serves as the border of the different operations. In this embodiment, the circuit elements of the array coil 400 are adjusted as described above by using the above characteristic of the parallel resonant circuit 500.

<Simulation Results>

Figure 9:
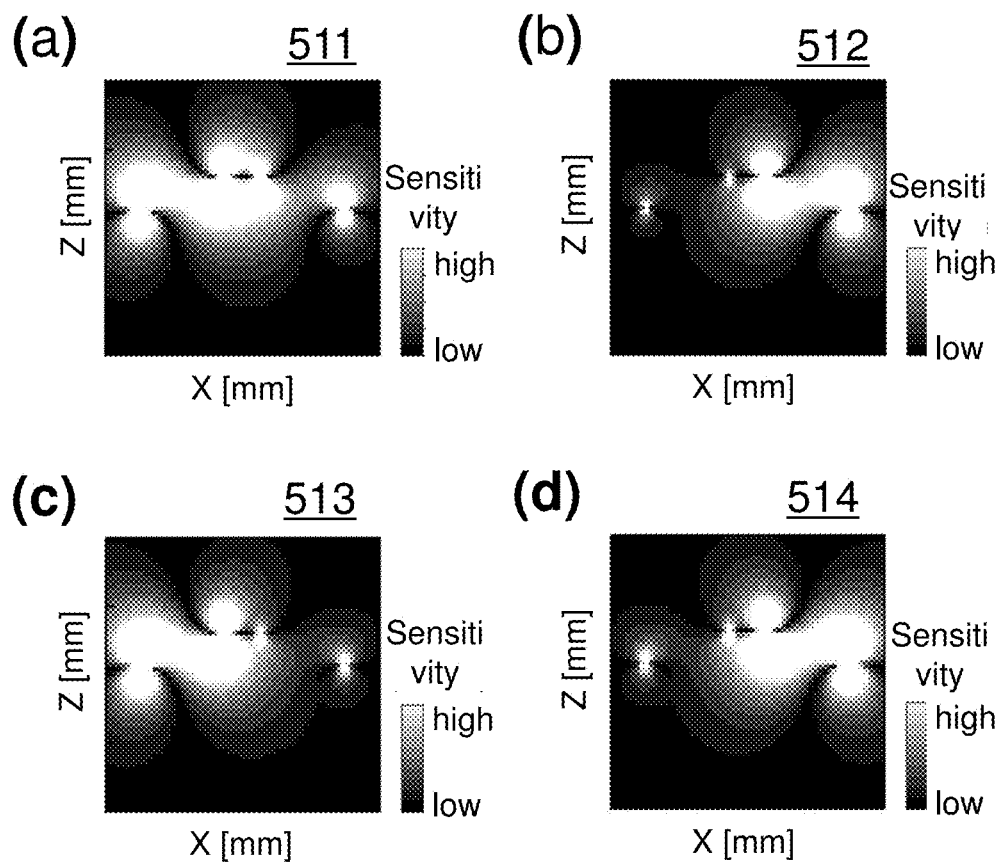
FIGS. 9a and 9b are explanatory drawings for explaining results of simulation of sensitivity map of the array coil of the first embodiment.
FIGS. 9c and 9d are explanatory drawings for explaining results of simulation of sensitivity map of a conventional array coil.
FIG. 9e is a graph showing sensitivity profiles of the array coil of the first embodiment, and the conventional array coil.
Figure 9:
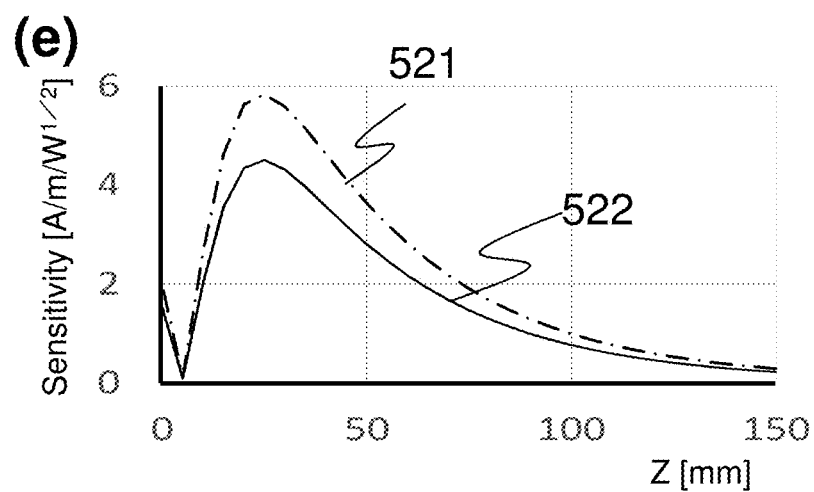

Results of calculation performed with an electromagnetic field simulator are shown in FIGS. 9a to 9e. FIGS. 9a and 9b show sensitivity profile 511 of the first subcoil 410A, and sensitivity profile 512 of the second subcoil 410B, respectively. FIGS. 9c and 9d show sensitivity profile 513 of the first channel (first subcoil 410A), and sensitivity profile 514 of the second channel (second subcoil 410B) of a conventional array coil (RF coil) of two channels, respectively.

FIG. 9e shows sensitivity profile 521 (dashed line) on the Z-axis obtained by synthesis of the sensitivities of the first subcoil 410A and the second subcoil 410B of this embodiment. In this case, the adjustment is performed so that the resonance frequency of the parallel resonant circuit formed by the adjustment inductor 641B ($L_{22}$) and the parallel capacitor 624B ($C_{24}$) ($L_{22}C_{24}$ resonant circuit) becomes 90 MHz, which is smaller than $f_0$. On the other hand, the solid line 522 is sensitivity profile of the conventional RF coil for the case where the magnetic coupling is eliminated.

As seen from these drawings, by the magnetic coupling, sensitivity area of the array coil 400 of this embodiment is expanded, and it shows high sensitivity in the region of the imaging subject (test subject) 103.

As explained above, the MRI apparatus 100 of this embodiment comprises a static magnetic field formation part for forming a static magnetic field, a gradient magnetic field formation part for forming a gradient magnetic field, a radio frequency magnetic field generation part for generating a radio frequency magnetic field, the transmitting coil 151 for irradiating the radio frequency magnetic field on a test subject, the receiving coil 161 for detecting a magnetic resonance signal from the test subject, and an image reconstruction part for reconstructing an image from the detected magnetic resonance signal. The receiving coil 161 comprises the first subcoil 410A that has the first loop coil part 420A consisting of a conductor and can transmit and receive a magnetic resonance signal and the second subcoil 410B that has the second loop coil part 420B consisting of a conductor and can transmit and receive a magnetic resonance signal. The first subcoil 410A is disposed and adjusted so that resonance frequency of the first subcoil 410A alone is different from nuclear magnetic resonance frequency as frequency of the magnetic resonance signal as the object of transmission and reception, and the first subcoil 410A magnetically couples with the second subcoil 410B to form circling electric current paths in loop of the first loop coil part and loop of the second loop coil part, and resonates at the nuclear magnetic resonance frequency. The transmitting coil 151 and the receiving coil 161 comprise magnetic coupling-preventing circuits 210 and 220 for preventing magnetic coupling between the transmitting coil 151 and the receiving coil 161, respectively.

The first subcoil 410A further comprises the first magnetic coupling-adjusting part 441A that connects the first loop coil part 420A and the first low impedance signal processing circuit 430A to which the first subcoil 410A is connected. The first loop coil part 420A comprises the first series capacitor 422A serially inserted with respect to inductor component of the loop 421A, and the first parallel capacitor 424A serially inserted with respect to the inductor component, which makes the first loop coil part 420A to be a parallel resonant circuit. The second subcoil 410B further comprises the second magnetic coupling-adjusting part 441B that connects the second loop coil part 420B and the second low impedance signal processing circuit 430B to which the second subcoil 410B is connected. The second loop coil part 420B comprises the second series capacitor 422B serially inserted with respect to inductor component of the loop 421B, and the second parallel capacitor 424B serially inserted with respect to the inductor component, which makes the second loop coil part 420B to be a parallel resonant circuit. The first magnetic coupling-adjusting part 441A comprises at least either one of a capacitor and inductor as a first adjustment circuit element. The second magnetic coupling-adjusting part 441B comprises at least either one of a capacitor and inductor as a second adjustment circuit element. The first subcoil 410A and the second subcoil 410B are adjusted by adjusting values of the first adjustment circuit element, second adjustment circuit element, first series capacitor 422A, second series capacitor 422B, first parallel capacitor 424A, and second parallel capacitor 424B.

The first subcoil 410 and the second subcoil are disposed at such positions that they can magnetically couple with each other.

The array coil 400 of this embodiment disposed and adjusted as described above is tuned at the nuclear magnetic resonance frequency $f_0$. At the time of signal reception, the first subcoil 410A shares the loop coil parts 420A and 420B with the second subcoil 410B, and detect a signal with an expanded sensitivity area, and thus the second subcoil 410B can detect a signal at high sensitivity without magnetically coupling with the first subcoil 410A. As described above, the array coil 400 of this embodiment can constitute sensitivity profile that cannot be obtained with two small surface coils, and efficiently (highly sensitively) obtain signals.

Further, the first subcoil 410A and the second subcoil 410B show different sensitivity profiles for the imaging region. Therefore, the array coil 400 of this embodiment can maintain the multi-channel characteristic that it is constituted by multiple coils showing different sensitivity profiles in the imaging region, and enables high-speed imaging.

Thus, the array coil 400 of this embodiment can realize both multi-channel characteristic, and large and deep sensitivity area. This multi-channel characteristic, the large sensitivity area, and high sensitivity are realized by adjustment of disposition and values of the circuit elements. Therefore, the configuration is not complicated, either. Further, since the MRI apparatus of this embodiment uses this array coil 400 as the receiving RF coil 161, it can obtain an image of high image quality at high speed.

<Other Examples of Low Impedance Signal Processing Circuit>

In the above explanation of this embodiment, the low input impedance signal amplifier 431 is used for the low impedance signal processing circuit 430. However, the circuit element used as the low impedance signal processing circuit 430 is not limited to this. For example, it may be a low input impedance conversion circuit, or the like. It is sufficient that it is such a circuit that, when the loop coil part 420 of the first subcoil 410A and the loop coil part 420 of the second subcoil 410B magnetically couple with each other, impedance of the second low impedance signal processing circuit 430 becomes low relative to the first subcoil 410A.

By changing the low impedance signal processing circuit 430, the array coil 400 to be developed can be optimized, and sensitivity can be improved.

<Other Examples of Adjustment of Mutual Inductance>

In the above explanation of this embodiment, magnitude of the mutual inductance M is adjusted by changing the positional relationship of the first subcoil 410A and the second subcoil 410B at the time of disposition thereof. However, means for adjusting the magnitude of the mutual inductance M is not limited to this.

Figure 10:
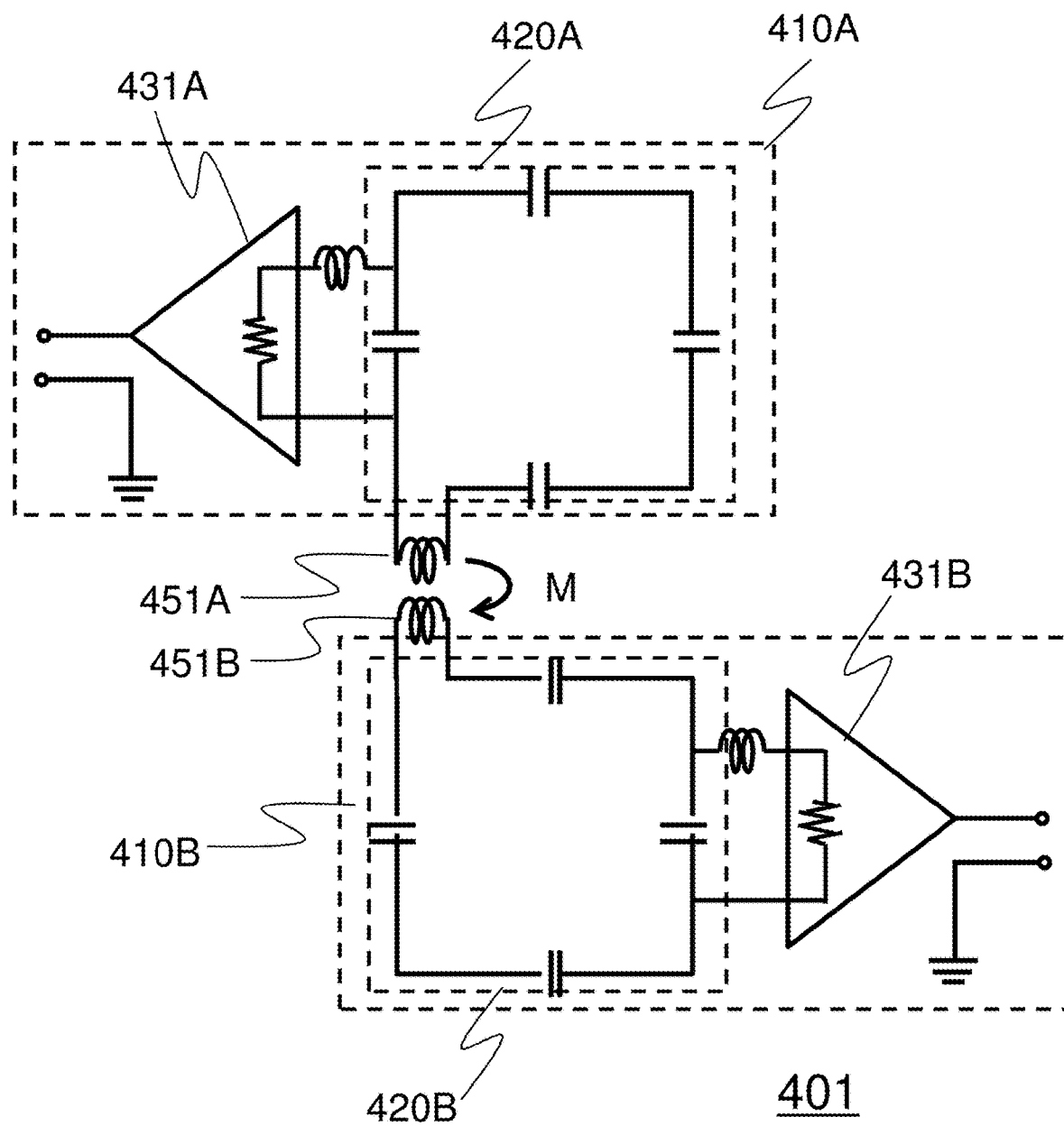
FIG. 10 is an explanatory drawing for explaining a modification of the first embodiment.

For example, a coupling inductor 451 may be disposed in a part of each loop 421 as shown in FIG. 10, and the magnetic coupling may be adjusted by using this.

That is, the first subcoil 410A further comprises a first coupling inductor 451A, and the second subcoil 410B further comprises a second coupling inductor 451B. And the first subcoil 410A and the second subcoil 410B are magnetically coupled by the first coupling inductor 451A and the second coupling inductor 451B.

The coupling inductor 451 may be provided in only one of the subcoils 410. The magnitude of the mutual inductance M can be freely adjusted by using the coupling inductor 451 irrespective of the disposition positions of the both subcoils 410.

Further, as shown in FIG. 10, a part of the loop 421 may be extended, and the coupling inductor 451 may be disposed at the end of the extended portion. With such a configuration, even if two of the subcoils 410A and 410B are disposed at comparatively distant positions, they can be magnetically coupled. Therefore, if the array coil 400 has the coupling inductor 451, restrictions on the disposition positions of the both subcoils 410 are reduced. For example, by disposing the both at distant positions, a large coil loop can be constituted as a whole, and thus deep part sensitivity is improved.

<Other Examples of Disposition Position of Subcoil>

For this embodiment, there has been explained a case where the array coil 400 is disposed in a plane having a small angle with respect to the plane perpendicular to the direction of the magnetic field. However, the disposition plane is not limited to such a plane. It may be disposed so that a rotating magnetic field formed by the array coil 400 in a region of interest in a direction perpendicular to the static magnetic field can be more efficiently detected or generated compared with each subcoil 410 alone. For example, the array coil 400 may be disposed in a plane having a small angle to the plane parallel to the direction of the magnetic field. Further, the first subcoil 410A may be disposed in a plane perpendicular to the direction of the magnetic field, and the second subcoil 410B may be disposed in a plane parallel to the direction of the magnetic field. By changing the disposition angle as described above, there is enabled detection or generation of a rotating magnetic field that cannot be realized by the subcoil 410 alone, and it becomes possible to acquire a magnetic resonance signal at high sensitivity for a region of interest.

For this embodiment, there has been explained an example in which the first subcoil 410A and the second subcoil 410B are disposed in planes each defined by rotating a plane perpendicular to the magnetic field by 20°. However, the disposition angle is not limited to this angle. The both may be disposed in the same plane, they may be disposed in planes perpendicular to each other, or they may be disposed in two parallel different planes. They may also be disposed so that a rotating magnetic field can be efficiently detected or generated using phase difference of the electric currents that flow in the loop 421A and loop 421B.

By changing the disposition angle, the disposition of the array coil 400 can be optimized, and it becomes possible to acquire a magnetic resonance signal at high sensitivity.

<Other Examples of Adjustment of Circuit Elements>

Although 90 MHz is used as the value smaller than $f_0$ (124 MHz) used for the adjustment of the resonance frequency of the $L_{22}C_{24}$ resonant circuit in the aforementioned example of the adjustment of this embodiment, the resonance frequency of the $L_{22}C_{24}$ resonant circuit may be of another value.

Figure 11:
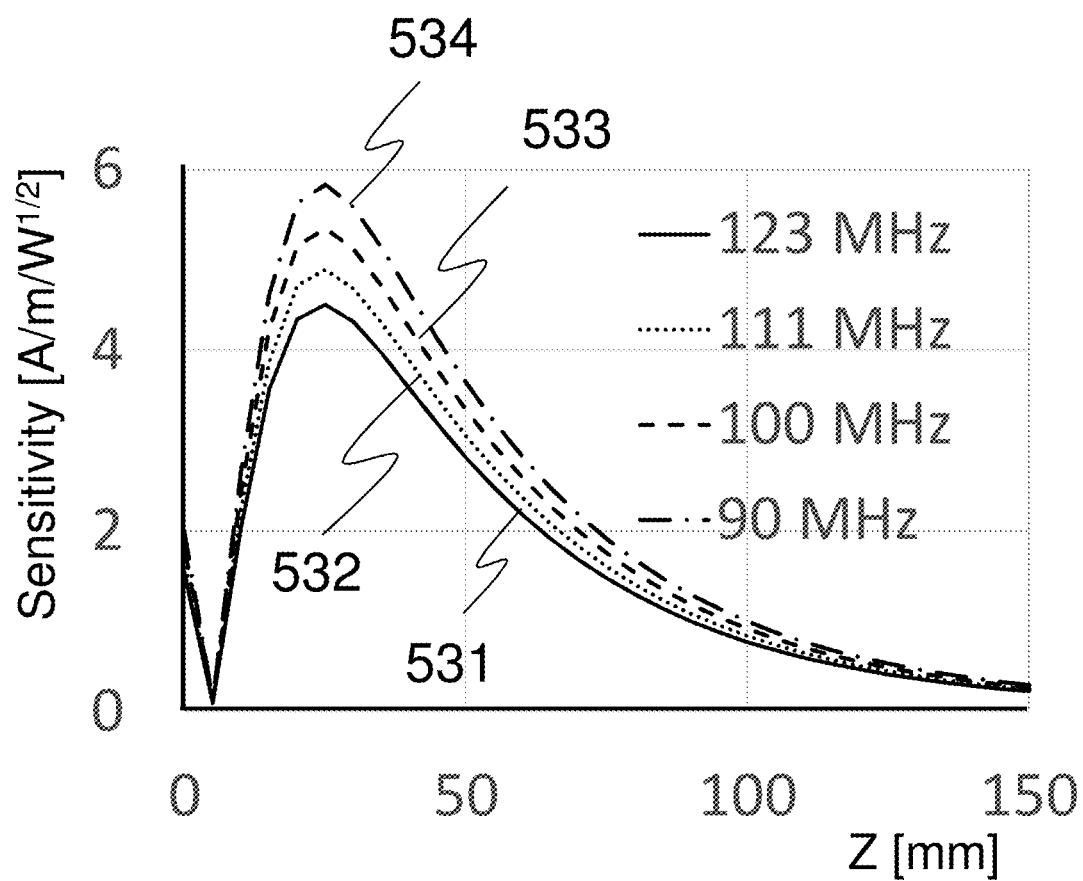
FIG. 11 is a graph of sensitivity profiles obtained with changing the resonance frequency used at the time of the adjustment in the first embodiment.

In FIG. 11, sensitivity profiles 531, 532, 533, and 534 for resonance frequencies of the $L_{22}C_{24}$ resonant circuit of 123 MHz, 111 MHz, 100 MHz, and 90 MHz are shown. They are sensitivity profiles on the Z-axis obtained by synthesizing the sensitivities of the first subcoil 410A and the second subcoil 410B of this embodiment. As shown in this drawing, sensitivity of the array coil 400 of this embodiment is increased by setting the resonance frequency of the $L_{22}C_{24}$ resonant circuit to be a frequency different from $f_0$. Magnitude of the difference of the resonance frequency of the $L_{22}C_{24}$ resonant circuit and $f_0$ is not limited. However, it is desirable that the resonance frequency of the $L_{22}C_{24}$ resonant circuit and $f_0$ differ by 10% or more.

That is, sensitivity of the array coil 400 of this embodiment can be increased by adjusting the resonance frequency of the $L_{22}C_{24}$ resonant circuit to a frequency different from $f_0$ (124 MHz) and intentionally making two of the subcoils 410 coupled.

It is also possible to set the resonance frequency of the $L_{22}C_{24}$ resonant circuit to be a frequency higher than $f_0$, and then adjust the circuit elements. By performing the adjustment in such a way, clockwise circling electric currents flow in both the first loop 421A and the second loop 421B, and distribution of electric current like that of a large surface coil can be formed by the first loop 421A and second loop 421B. Also in this case, by changing the resonance frequency to change coupling magnitude, sensitivity of the array coil 400 can be increased as in the case where the resonance frequency is set to be a frequency lower than $f_0$.

When the loops 421 are disposed so that the coupling coefficients of the first loop 421A and the second loop 421B has positive and negative codes opposite to those of the above examples of this embodiment, the relation between the resonance frequency and the flow of electric current is reversed. That is, when the resonance frequency of the resonant circuit of $L_{22}C_{24}$ is higher than $f_0$ (124 MHz), an electric current path like that of a butterfly coil is effectually formed, and when it is lower than $f_0$, a current distribution like that of a large surface coil is effectually formed.

As described above, the resonance frequency of the $L_{22}C_{24}$ resonant circuit is not severely restricted at the time of the adjustment of the circuit elements. Therefore, degree of freedom for design of the loop 421 of the array coil 400 of this embodiment is high.

<Other Examples of Size and Shape of Subcoils>

In the above explanations of this embodiment, loops of the same size and shape are used as the first loop 421A and the second loop 421B. However, the both may have different shapes and/or different sizes. Use of the loops 421 of different shapes and/or sizes increases degree of freedom for disposition pattern. Reduction of restrictions on the shape and/or size of the loops 421 makes adjustment of the magnitude of the magnetic coupling easier, and thus improves sensitivity.

In the above explanations of this embodiment, coils of the same shape are used for the first subcoil 410A and the second subcoil 410B. However, combination of shape and size is not limited to such a configuration, and they may be different. By using different shapes in combination, an optimal coil suitable for an imaging subject (test subject)

103 can be realized, and magnitude of the magnetic coupling can also be adjusted. In the above examples, three of capacitors are inserted into the loop 421 of the loop coil part 420, but this embodiment is not limited to such a configuration. It is sufficient that at least one capacitor is inserted.

<Modifications of Shape of Coil Part>

This embodiment has been explained above for an example wherein the loop 421 of each subcoil 410 is a rectangular or circular single loop substantially in a plane. However, the shape of the loop 421 is not limited to these. Any one that provides an equivalent circuit equivalent to the equivalent circuit 600 can be used.

Figure 12:
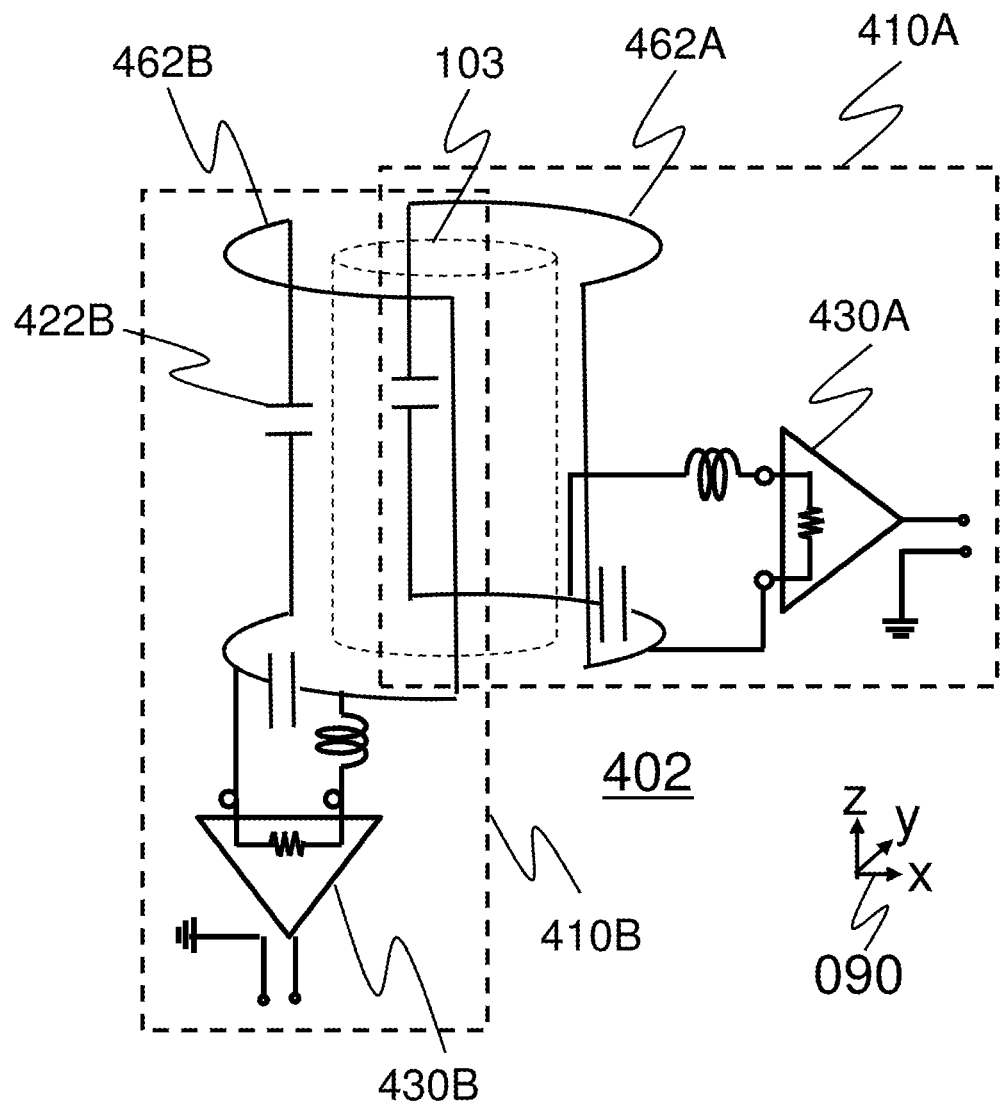
FIG. 12 is an explanatory drawing for explaining a modification of the first embodiment.

For example, as shown in FIG. 12, the first loop 462A and the second loop 462B may have a saddle shape, which are disposed so as to face each other in a cylindrical shape. An array coil (saddle-shaped array coil) 402 comprising saddle-shaped loops is shown in FIG. 12. In the drawing, the z-axis direction of the coordinate system 090 is the direction of the static magnetic field.

Figure 13:
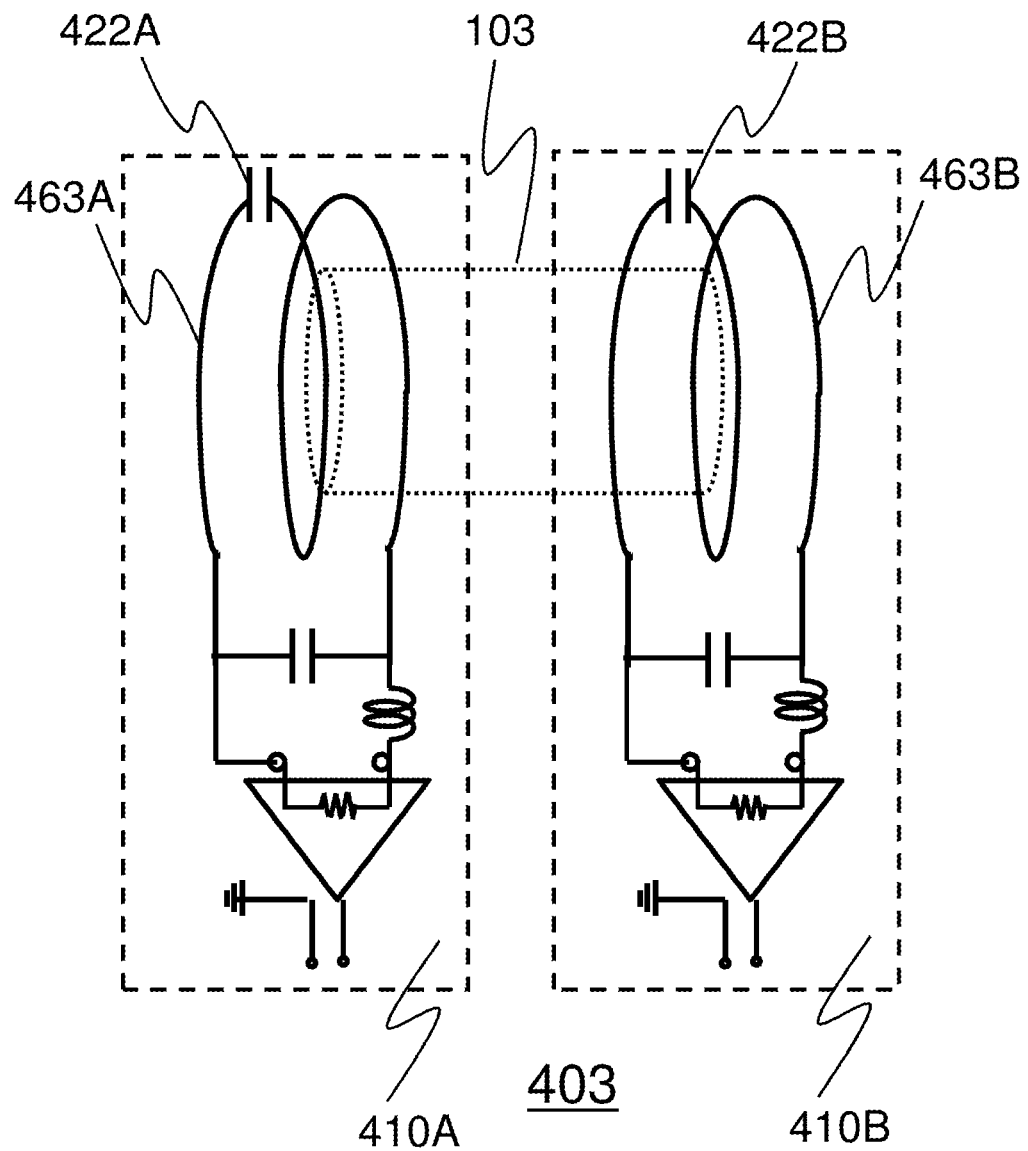
FIG. 13 is an explanatory drawing for explaining a modification of the first embodiment.

As shown in FIG. 13, the first loop 463A and the second loop 463B may also have a solenoid coil shape, and they may be disposed adjacently to each other. An array coil (solenoid coil-shaped array coil) 403 comprising solenoid coil-shaped loops is shown in FIG. 13. In the drawing, the z-axis direction of the coordinate system 090 is the direction of the static magnetic field.

Since these array coils 402 and 403 differ from the aforementioned array coil 400 in the shape and mutual inductance of loops, values of the parallel capacitor, series capacitor, and adjustment inductor are accordingly adjusted. The adjustment is performed so that the equations (2) to (5) are satisfied as in the aforementioned examples.

Since each of the saddle-shaped array coil 402 and solenoid coil-shaped array coil 403 is represented by an equivalent circuit 600, the operation principles thereof are the same as that of the array coil 400 of this embodiment. That is, the loops 462A and 463A of the first subcoil 410A couple with the loops 462B and 463B of the second subcoil 410B, and operate. On the other hand, the second subcoil 410B independently operates.

Since adjustment is performed as described above, each subcoil 410 that constitutes the saddle-shaped array coil 402 or solenoid-shaped array coil 403 show sensitivity to a magnetic resonance signal as the object of the detection. Further, since the loops 462A and 463A of the first subcoil 410A couple with the loops 462B and 463B of the second subcoil 410B by magnetic coupling, they can be regarded as a large coil loop, and the sensitivity area is expanded. The second subcoil 410B does not couple with the first subcoil 410A, and has a sensitivity area. Therefore, sensitivity profiles of the both subcoils in an imaging region differ from each other, and the number of channels can be maintained. Therefore, the array coils 402 and 403 showing a large sensitivity area can be realized with maintaining the number of channels.

Since the loop 462 of the saddle-shaped array coil 402 has a saddle shape, a test subject 103 such as arm, leg, and body of an imaging subject is placed in the saddle-shaped loop 462 as shown in FIG. 12. Magnetic resonance signals from a region remote along the depth direction, in addition to signals from the surface of the test subject 103, can be thereby detected at high sensitivity.

Since the loop 463 of the solenoid-shaped array coil 403 has a solenoid shape, a test subject 103 such as arm, leg, and body of an imaging subject is placed in the solenoid-shaped loop 463 as shown in FIG. 13. Two kinds of magnetic resonance signals, signals from the surface of the test subject 103, and in addition, signals from a region remote along the depth direction can be thereby detected at high sensitivity and with uniform distribution. The solenoid-shaped array coil 403 has a uniform sensitivity profile in a larger region compared with that of the saddle-shaped array coil 402.

Also for these modifications, examples where one series capacitor 422 is disposed in the loops 462 and 463 is exemplified. However, the number of the capacitor to be inserted is not limited, as in the aforementioned examples. A plurality of series capacitors may be inserted.

In these modifications, loops of the same shape and same size are used for the first loops 462A and 463A, and the second loop 462B and 463B. However, sizes and/or shapes of the both may be different. Use of loops of different shapes and/or sizes for each of the first subcoil 410A and the second subcoil 410B increases degree of freedom for disposition pattern. Adjustment of the magnitude of the magnetic coupling is also made easier.

<Modifications of Magnetic Coupling>

In the aforementioned examples and modifications, among two of the subcoils 410, the first subcoil 410A magnetically couples with the second subcoil 410B, but the second subcoil 410B does not magnetically couple with the first subcoil 410A at the time of signal reception. However, they may also be configured so that all the subcoils 410 magnetically couple with the other ones, respectively, at the time of signal reception.

That is, the second subcoil 410B may be adjusted so that the resonance frequency of the second subcoil 410B alone is different from the nuclear magnetic resonance frequency, the second subcoil 410B magnetically couples with the first subcoil 410A, circling electric current paths are thereby formed in the first loop 421A and the second loop 421B, and it resonates at the nuclear magnetic resonance frequency.

Figure 14:
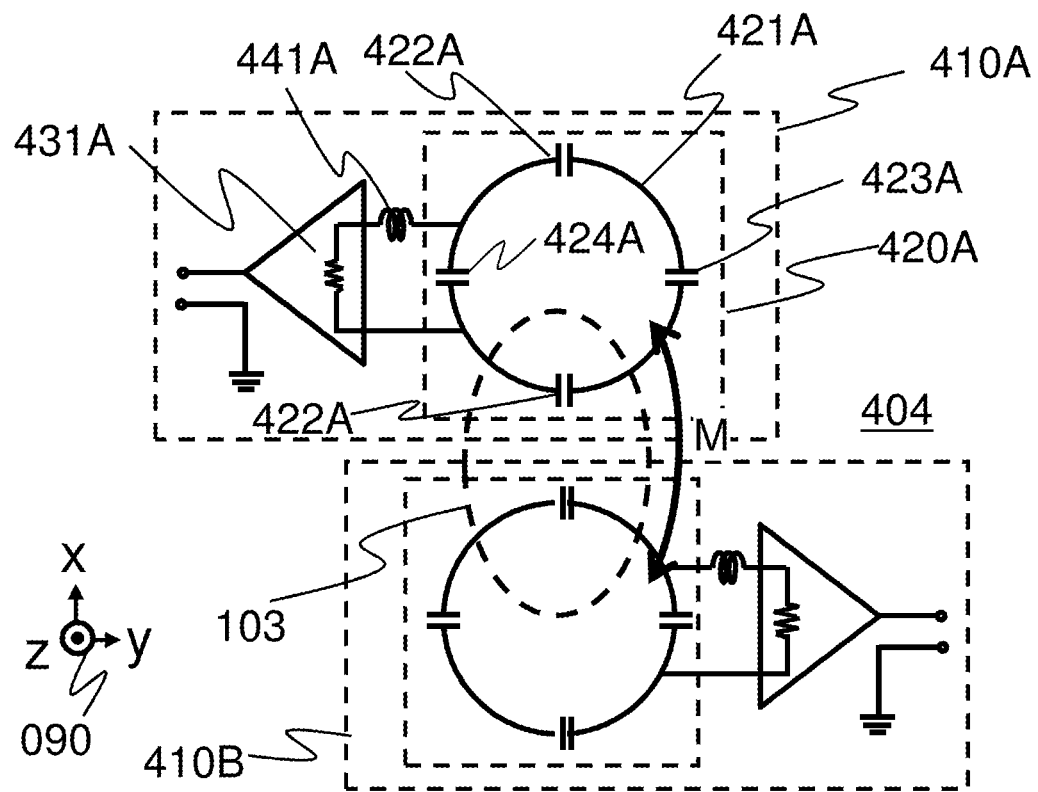
FIG. 14 is an explanatory drawing for explaining a modification of the first embodiment.
Figure 15:
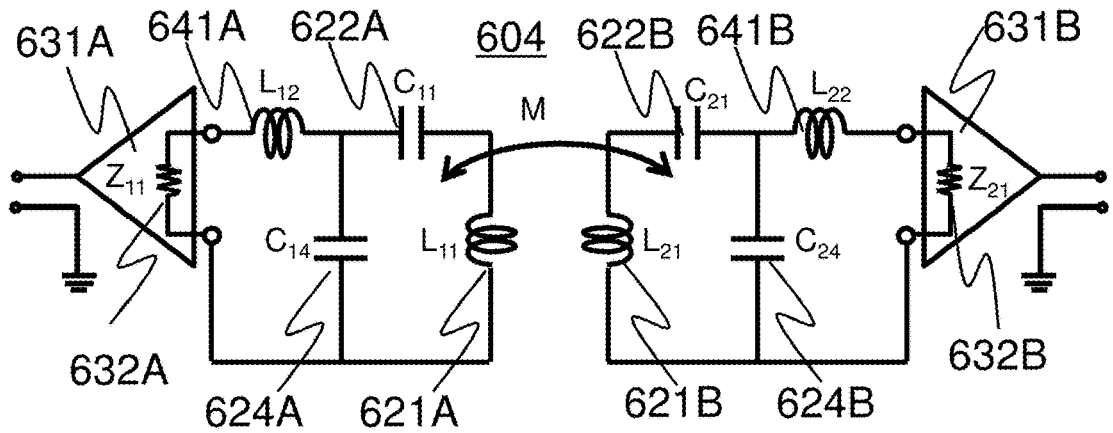
FIGS. 15a to 15c are explanatory drawings for explaining operation of a modification of the first embodiment.
Figure 15:
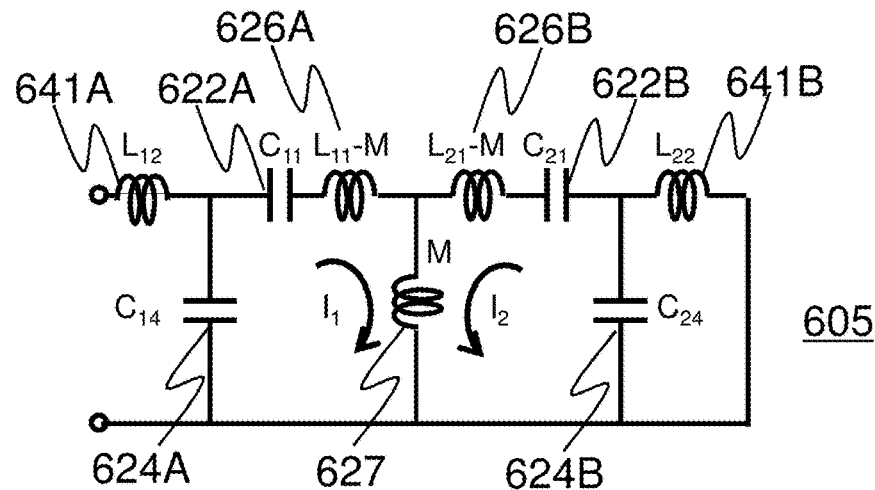
Figure 15:
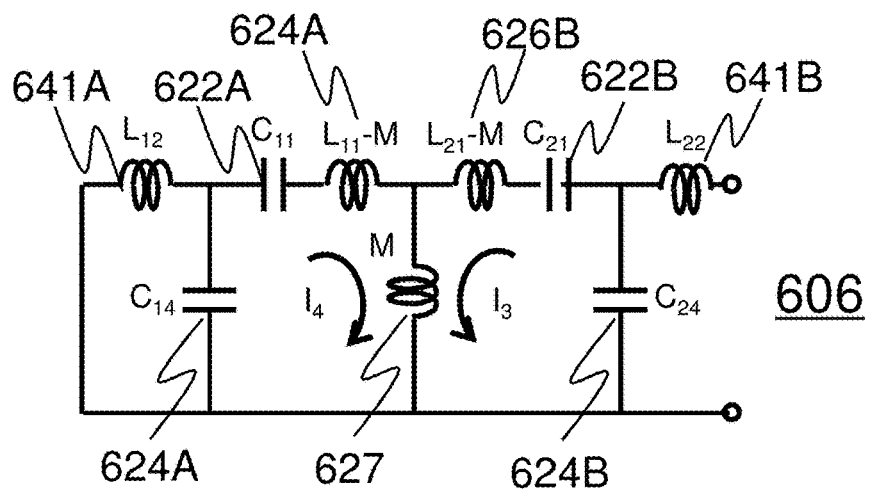

As shown in FIG. 14, the configuration of array coil 404 of this modification is the same as the configuration of the array coil 400 of this embodiment. However, the method for adjusting values of the constituent circuit elements (adjustment inductor 441, series capacitor 422, and parallel capacitor 424) is different. Hereafter, the method for adjusting values of the circuit elements of the array coil 404 will be explained with reference to an equivalent circuit 604 of the array coil 404 shown in FIG. 15.

The capacitors, values thereof, inductors, values thereof, and resonance frequencies of the circuits are henceforth referred to with the same numerals and codes as those used for the equivalent circuit 600 in the aforementioned example.

In order to realize both high sensitivity and multi-channel characteristic, values of the circuit elements that constitute the array coil 404 are adjusted so that the following equations (11) to (15) are satisfied.

$$f_{11} = f_{22} = f_0 \quad (11)$$

$$f_{10} \neq f_0 \quad (12)$$

$$f_{20} \neq f_0 \quad (13)$$

[Equation 14]

$$\frac{1}{2\pi\sqrt{L_{22}C_{24}}} \neq f_0 \quad (14)$$

$$\frac{1}{2\pi\sqrt{L_{12}C_{14}}} \neq f_0 \quad (15)$$

If the circuit elements are adjusted in accordance with the equation (14), the resonance frequency of the $L_{22}C_{24}$ resonant circuit of the second subcoil 410B (610B) differs from the nuclear magnetic resonance frequency $f_0$. Therefore, at the time of signal reception, resistance between the both ends of the capacitor 424B of the second subcoil 410B does not become high, and it magnetically couples with the first subcoil 410A.

An equivalent circuit 605 of the first resonance part of the first subcoil 410A in a state that the first loop coil part 420A and the second loop coil part 420B are magnetically coupled by the aforementioned adjustment is shown in FIG. 15b. That is, at the time of signal reception, the first resonance part of the first subcoil 410A serves as the circuit 605 in which the first loop coil part 420A and the second loop coil part 420B are coupled by magnetic coupling as shown in FIG. 15b.

If the circuit elements are adjusted in accordance with the equation (15), the resonance frequency of the $L_{12}C_{14}$ resonant circuit of the second subcoil 410A (610A) differs from the nuclear magnetic resonance frequency $f_0$. Therefore, at the time of signal reception, resistance between the both ends of the capacitor 424A of the first subcoil 410A does not become high, and it magnetically couple with the second subcoil 410B.

An equivalent circuit 606 of the second resonance part of the second subcoil 410B in a state that the first loop coil part 420A and the second loop coil part 420B are magnetically coupled by the aforementioned adjustment is shown in FIG. 15c. That is, at the time of signal reception, the second resonance part of the second subcoil 410B serves as the circuit 606 in which the first loop coil part 420A and the second loop coil part 420B are coupled by magnetic coupling as shown in FIG. 15c.

If the circuit elements are adjusted in accordance with the equations (12) and (13), resonance frequencies $f_{10}$ and $f_{20}$ of the first subcoil 410A and second subcoil 410B each alone differ from the nuclear magnetic resonance frequency $f_0$.

If the circuit elements are adjusted in accordance with the equation (11), resonance frequency $f_{11}$ of the first resonance part and resonance frequency $f_{22}$ of the second resonance part at the time of signal reception come to be equal to the nuclear magnetic resonance frequency $f_0$. As a result, the subcoil 410A and subcoil 410B can detect a magnetic resonance signal in a state that they are magnetically coupled.

The adjustment of the circuit elements is explained with reference to a specific example in which the nuclear magnetic resonance frequency $f_0$ is, for example, 124 MHz, which is the nuclear magnetic resonance frequency of hydrogen at a static magnetic field intensity of 3 T (Tesla).

The circuit elements are adjusted so that the equivalent circuits 605 and 606 shown in FIGS. 15b and 15c resonate at 124 MHz, and impedance between the both ends of the series circuit of the inductor 641A and the parallel capacitor 624A ($C_{14}$) becomes 50Ω, as in the aforementioned examples. And value of the adjustment inductor 641 and value of the parallel capacitor 624 are adjusted on the basis of the characteristic principle of parallel resonant circuit so that the aforementioned equations are satisfied, and the electric currents flow in an intended manner at the time of coupling.

In the case of this modification, either of the first subcoil 410A and the second subcoil 410B may be adjusted first.

Since adjustment of values of circuit elements of one subcoil 410 affects the resonance characteristic of the other subcoil 410, the adjustment is performed by repeating adjustment of values of circuit elements of each subcoil 410 several times so that the first subcoil 410A and the second subcoil 410B resonate at 124 MHz.

When the value smaller than $f_0$ is defined to be 90 MHz, the parameters adjusted by the aforementioned adjustment are, for example, as follows: $C_{11}$=7.7 pF, $C_{14}$=148 pF, $C_{21}$=98 pF, $C_{24}$=7.9 pF, $L_{12}$=11 nH, and $L_{22}$=26 nH.

If the adjustment is performed as described above, the array coil 404 of this modification resonates at the nuclear magnetic resonance frequency, and receives magnetic resonance signals.

The first subcoil 410A shares the second loop 421B to expand the sensitivity area, and the second subcoil 410B shares the first loop 421A to expand the sensitivity area.

As described above, the subcoils that constitute the array coil 404 have sensitivity for the magnetic resonance signals to be received. At the same time, the first subcoil 410A magnetically couples with the second loop 421B, therefore they can be regarded as a large coil loop, and thus the sensitivity area is expanded. Specifically, since they show a sensitivity map similar to that of a butterfly coil, deep part sensitivity can be obtained. Similarly, since the second subcoil 410B is coupled with the first loop 421A by magnetic coupling, they can be regarded as a large coil loop, and thus the sensitivity area is expanded. Specifically, since they shows a sensitivity map similar to that of a butterfly coil, deep part sensitivity can be obtained.

The sensitivity profiles of the both subcoils in the imaging area differ from each other. Therefore, the array coil 404 of this modification can operate as an array coil showing a large sensitivity area and high sensitivity without reducing the number of channels. Therefore, since it becomes an array coil of coils showing a large sensitivity area though it is a multi-channel coil, the subcoils of the array coil 404 of this modification magnetically couple with one another, and thus multi-channel characteristic and large and deep sensitivity area are reconciled. Further, since this effect is realized by disposition of the subcoils 410, and adjustment of values of the circuit elements, the structure is not complicated, either.

In the above modification of this embodiment, the same values (90 MHz) are used as the resonance frequencies of the $C_{12}L_{14}$ resonant circuit and the $L_{22}C_{24}$ resonant circuit at the time of the adjustment of the circuit elements, but this embodiment is not limited to such a configuration. The values may differ from each other. If different values are used for them, electric currents that flow in the partners of the magnetic coupling change, and therefore design of the sensitivity area appropriate for the purpose is enabled. Although magnitude of the differences of the resonance frequencies of these resonant circuits and $f_0$ are not limited, it is desirable that the resonance frequency of $L_{22}C_{24}$ resonant circuit and $f_0$ differ by 10% or more.

Second Embodiment

Hereafter, the second embodiment of the present invention will be explained. In the first embodiment, the array coil is constituted by a combination of two of subcoils. In this embodiment, an array coil is constituted by a combination of three or more subcoils to realize multi-channel characteristic, large sensitivity area, and high sensitivity, and an example thereof is explained. Use of a plurality of coils can improve the sensitivity.

The MRI apparatus of this embodiment basically has the same configuration as that of the MRI apparatus 100 of the first embodiment. Hereafter, this embodiment will be explained by focusing the explanation on configurations different from those of the first embodiment.

Figure 16:
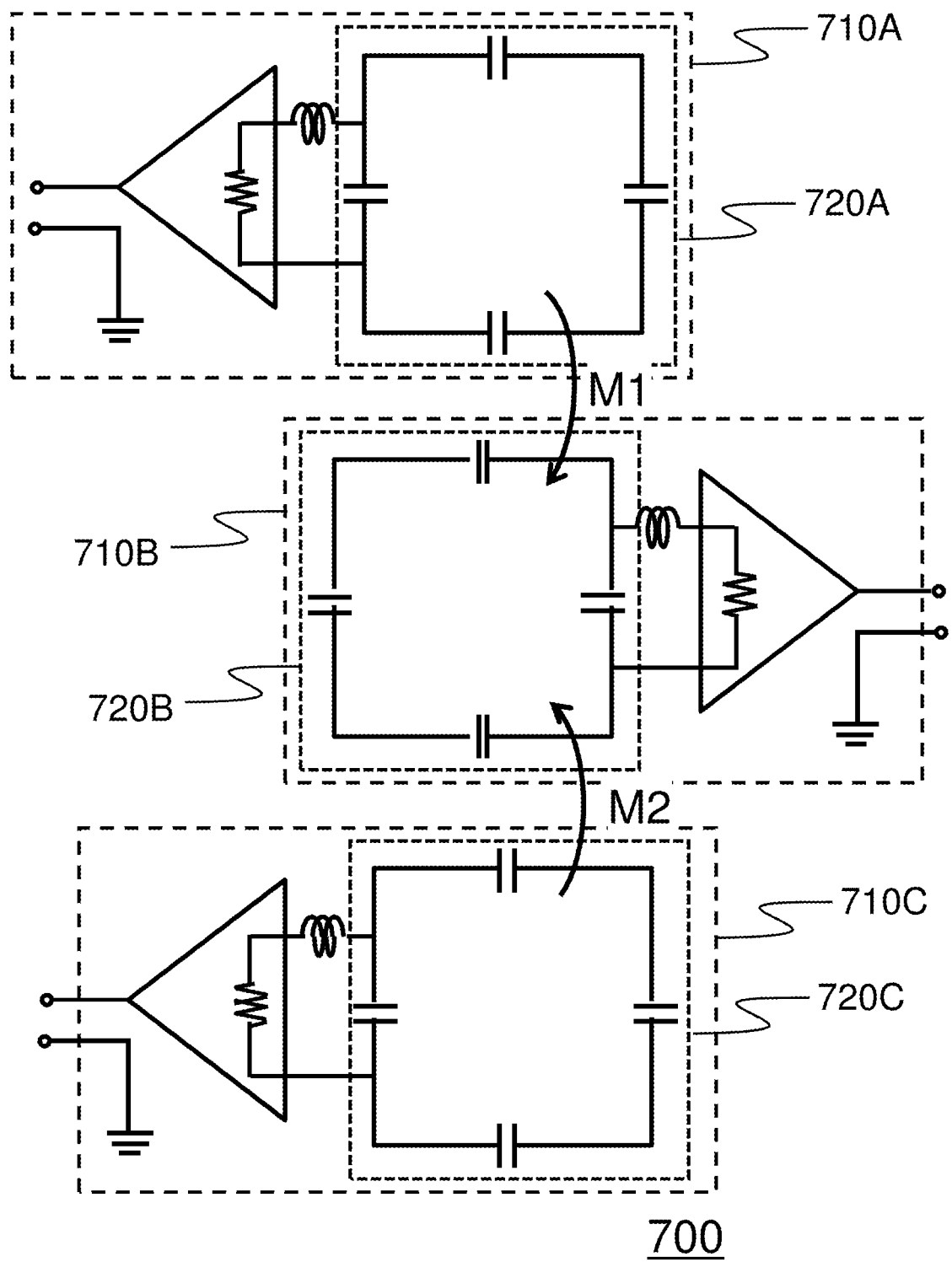
FIG. 16 is an explanatory drawing for explaining the array coil of the second embodiment.

FIG. 16 is a drawing for explaining an array coil 700 of this embodiment. As shown in this drawing, the array coil 700 of this embodiment comprises a first subcoil 710A, second subcoil 710B, and third subcoil 710C. These are disposed in this order at such positions that adjacent channels (subcoils 710) can magnetically couple with each other.

The configurations of the first subcoil 410A and the third subcoil 710C are the same as that of the first subcoil 410A of the first embodiment. The second subcoil 410B is the same as the second subcoil 410B of the first embodiment. As in the first embodiment, each capacitor and inductor are adjusted so that the equations (2) to (5) are satisfied.

That is, the radio frequency coil (array coil 700) of this embodiment comprises, in addition to the first subcoil 710A and second subcoil 710B, the third loop coil part 720A in the first subcoil 710A and second subcoil 710B, and further comprises the third subcoil 710C that can transmit and receive a magnetic resonance signal, and the third subcoil 710C is adjusted so that the resonance frequency of the third subcoil 710C alone is different from the nuclear magnetic resonance frequency, the third subcoil 710C magnetically couples with the second subcoil 710B, as a result, circling electric current paths are formed in the loop of the third loop coil part 720C and the loop of the second loop coil part 720B, and they resonate at the nuclear magnetic resonance frequency.

First, the subcoils 710A, 710B, and 710C of this embodiment are adjusted so as to resonate at the nuclear magnetic resonance frequency of the atom as the object of detection. For example, they are adjusted so as to resonate at 124 MHz, which is the nuclear magnetic resonance frequency of hydrogen at a static magnetic field intensity of 3 T (Tesla). And the circuit elements of the second subcoil 710B are adjusted so that the $C_{22}L_{23}$ resonant circuit should not resonate at the nuclear magnetic resonance frequency. That is, they are adjusted so that the circuit should not become highly resistant at the time of reception of signals of this frequency. The first subcoil 710A and third subcoil 710C are adjusted so that the $C_{12}L_{14}$ resonant circuit resonates at the nuclear magnetic resonance frequency, and becomes highly resistant at the time of reception of signals of this frequency.

The loop coil part 720A of the first subcoil 710A magnetically couples with the loop coil part 720B of the second subcoil 710B at the time of signal reception. This is because the first subcoil 710A and the second subcoil 710B are disposed at such positions that they can magnetically couple with each other, the circuit elements of the second subcoil 710B are adjusted in accordance with aforementioned equation (4), and therefore the circuit does not show high resistance at the time of signal reception (magnetic coupling is not eliminated). Hereafter, magnitude of mutual inductance of the first subcoil 710A and the second subcoil 710B is represented by M1.

On the other hand, the first loop coil part 720A hardly magnetically couples with the loop coil part 720C of the third subcoil 710C. The reverse is also the case. This is because the both are remote from each other, and the $C_{12}L_{14}$ resonant circuit resonates at the nuclear magnetic resonance frequency, and becomes highly resistant at the time of reception of signals of this frequency.

Similarly, the third the loop coil part 720C magnetically couples with the second loop coil part 720B at the time of signal reception. This is because the third subcoil 710C and the second subcoil 710B are disposed at such positions that they can magnetically couple with each other, in addition, the circuit elements of the second subcoil 710B are adjusted according to the aforementioned equation (4), and therefore it does not become highly resistant at the time of signal reception (elimination of magnetic coupling is not performed). Magnitude of the mutual inductance of the third subcoil 710C and the second subcoil 710B in this case is represented by M2.

The second loop coil part 720B does not magnetically couple with the first loop coil part 720A and the third loop coil part 720C at the time of signal reception. This is because the circuit elements of the first subcoil 710A and the third subcoil 710C are adjusted according to the aforementioned formula (5), and thus the both become highly resistant at the time of signal reception.

Therefore, at the time of signal reception, the first loop coil part 720A of the first subcoil 710A of the array coil 700 of this embodiment magnetically couples with the second loop coil part 720B of the same, and the first subcoil 710A thereby effectually forms an electric current path similar to that of a butterfly coil. The second subcoil 710B does not magnetically couple with any subcoil at the time of signal reception, and therefore forms an electric current path of common surface coil. At the time of signal reception, the third the loop coil part 720C of the third subcoil 710C magnetically couples with the second loop coil part 720B, and therefore the third subcoil 710C effectually forms an electric current path like that of a butterfly coil.

Accordingly, each subcoil 710 resonates at the nuclear magnetic resonance frequency of the object of the detection. Further, the first subcoil 710A and the third subcoil 710C magnetically couple with the second subcoil 710B at the time of signal reception, and effectually form an electric current path like that of a butterfly coil. Therefore, they show a large and deep sensitivity area. On the other hand, the second subcoil 710B does not magnetically couple with any other subcoil 710 at the time of signal reception. Therefore, the subcoils 710 show different sensitivity profiles to the region of interest.

Therefore, the array coil 700 of this embodiment realizes a large sensitivity area, high sensitivity, and multi-channel characteristic.

<Modification for Number of Subcoil>

This embodiment has been explained above with reference to an example where three of the subcoils 710A, 710B, and 710C are combined. However, the number of the subcoils 710 is not limited to this number. Four or more subcoils 710 may be used. By increasing the number of subcoils 710, sensitivity can be given in a larger region.

<Modification for Magnetic Coupling Pattern>

In the above example of this embodiment, the circuit elements are adjusted so that the first subcoil 710A couples with the second subcoil 710B, the third subcoil 710C couples with the second subcoil 710B, and the second subcoil 710B does not couple with any subcoil at the time of signal reception.

However, the pattern of magnetic coupling is not limited to such a configuration. For example, the circuit elements may be adjusted so that the first subcoil 710A and the second subcoil 710B magnetically couple with the third subcoil 710C, and the third subcoil 710C does not couple with any of them. The circuit elements may also be adjusted so that the second subcoil 710B and the third subcoil 710C magnetically couple to the first subcoil 710A, and the first subcoil 710A does not couple with any of them.

Further, the configuration may also be such a configuration that the first subcoil 710A couples with the second subcoil 710B, the second subcoil 710B couples with the third subcoil 710C, and the third subcoil 710C does not couple with any of the subcoils 710. In this case, there may be provided a magnetic coupling eliminating means such as partial overlapping of the loop coil parts 720 to eliminating magnetic coupling so that the third subcoil 710C does not magnetically couple with the first subcoil 710A and the second subcoil 710B. A sensitivity profile different from that of the aforementioned example of this embodiment can be thereby realized, and thus degree of freedom for design of sensitivity area is increased.

This embodiment has been explained above with reference to an example wherein the circuit elements are adjusted with supposing that magnetic coupling occurs in one direction. However, this embodiment is not limited to such a configuration. Like the modification of the first embodiment, the circuit elements may be adjusted so that the second subcoil 710B also magnetically couples with the first and third subcoils 710A and 710C.

With any of the coupling schemes, the array coil 700 of this embodiment and the array coils as modifications thereof can be operated as an array coil showing a large sensitivity area without reducing the number of channels. Since this characteristic is realized by disposition of each subcoil 710, and adjustment of values of the circuit elements, the structure is not complicated, either. Therefore, with the array coil 700 of this embodiment, both multi-channel characteristic and a large and deep sensitivity area can be realized with a simple configuration. Further, with the MRI apparatus of this embodiment using the array coil 700 as the receiving RF coil 161, an image of high image quality can be obtained at high speed.

According to this embodiment, combination of subcoils to be magnetically coupled can be freely selected, and therefore various kinds of sensitivity profiles can be realized by the selection. Therefore, the degree of freedom for design of sensitivity area is increased.

The modifications of the first embodiment such as those for type of circuit element used for the low impedance signal processing circuit, resonance frequency used at the time of adjustment of circuit elements, disposition position of each subcoil, presence or absence of coupling inductor, shape of loop, and size of each subcoil can also be applied to this embodiment.

Third Embodiment

Hereafter, the third embodiment of the present invention will be explained. In this embodiment, adjacent subcoils are disposed so that they partially overlap with each other to prevent magnetic coupling between the subcoils.

The MRI apparatus of this embodiment basically has the same configuration as that of the MRI apparatus 100 of the first embodiment. Hereafter, this embodiment will be explained by focusing the explanation on configurations different from those of the first embodiment.

Figure 17:
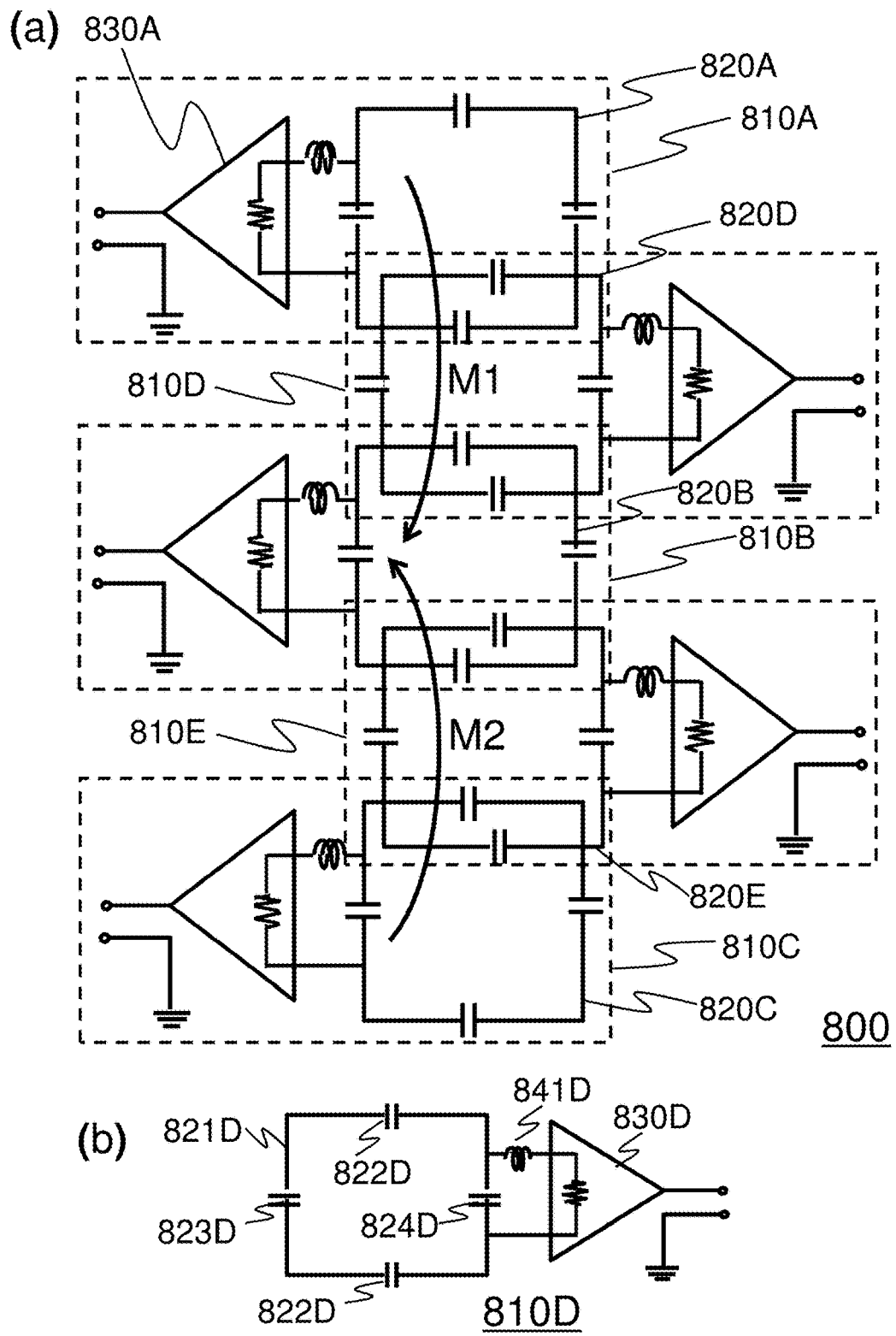
FIGS. 17a and 17b are explanatory drawings for explaining the array coil of the third embodiment.

FIGS. 17*a* and 17*b* are drawings for explaining an array coil 800 of this embodiment. Hereafter, this embodiment will be explained with reference to an example where the array coil 800 is constituted with five subcoils 810. However, the number of the subcoils 810 that constitute the array coil 800 is not limited to this number.

The array coil 800 comprises a first subcoil 810A, fourth subcoil 810D, second subcoil 810B, fifth subcoil 810E, and third subcoil 810C from the top.

Configuration of each subcoil 810 is the same as that of the subcoil 410 of the first embodiment. That is, each subcoil 810 further comprises a first magnetic coupling-adjusting part 841 that connects a loop coil part 820 and a first low impedance signal processing circuit 830 to which the subcoil 810 is connected, and the first loop coil part 820 comprises a first series capacitor 822 serially inserted with respect to inductor component of the loop 821, and a first parallel capacitor 824 inserted in parallel with respect to the inductor component, which makes the first loop coil part 820 to be a parallel resonant circuit.

As shown in this drawing, the subcoils 810 are disposed so that the loops 821 of the loop coil parts 820 of the adjacent subcoils 810 partially overlap with each other. In this configuration, overlapping area is determined so that magnetic coupling between the adjacent subcoils 810 is eliminated. That is, the adjacent subcoils 810 are disposed so that magnetic coupling of them is eliminated.

That is, in the array coil 800 of this embodiment, for example, the fourth loop coil part 820D is disposed so as to have overlapping regions overlapping with the first loop coil part 820A and the second loop coil part 820B, and the areas of the overlapping regions are determined so that the fourth subcoil 810D does not magnetically couple with the first subcoil 810A and the second subcoil 810B.

The fifth coil part 820E is also similarly disposed so as to have overlapping regions overlapping with the second loop coil part 820B and the third the loop coil part 820C, and the areas of the overlapping regions are determined so that the fifth subcoil 810E does not magnetically couple with the second subcoil 810B and the third subcoil 810C.

[Adjustment of Circuit Elements]

The circuit elements of the first subcoil 810A, second subcoil 810B, and third subcoil 810C are adjusted basically in the same manner as that used for the modification of the second embodiment in which each subcoil 810 magnetically couples with the adjacent subcoil at the time of signal reception. Hereafter, adjustment of the circuit elements of the fourth subcoil 810D and the fifth subcoil 810E will be explained by exemplifying that of the fourth subcoil 810D with reference to FIG. 17*b*.

Values of the series capacitors 822D ($C_{12}$) and 823D ($C_{13}$) are adjusted so that the circuit corresponding to the fourth subcoil 810D from which the low impedance signal processing circuit 830D is removed resonates at the nuclear magnetic resonance frequency $f_0$ of the detection object (124 MHz in the case of hydrogen), and the impedance between the both ends of the series circuit of the inductor 641A and the parallel capacitor 624A ($C_{14}$) becomes 50Ω. The adjustment inductor 841D ($L_{22}$) is adjusted so that the circuit of the loop coil part 820D except for the loop shows high impedance at $f_0$ (124 MHz in the case of hydrogen).

The circuit elements of the fifth subcoil 810E are adjusted similarly.

The circuit elements of the array coil 800 of this embodiment are adjusted as described above. The fourth subcoil 810D and the fifth subcoil 810E, which are disposed between the subcoils used in the second embodiment, are thereby made to resonate at 124 MHz, and made to be able to perform magnetic resonance signal acquisition operation, in addition to the operations of the second embodiment.

According to this embodiment, on the basis of the aforementioned characteristics, a larger number of coils can be disposed, and effect of improvement in sensitivity can be obtained, in addition to the effect of the second embodiment. The degree of freedom for design of sensitivity area is also improved, and thus sensitivity is improved.

Although this embodiment has been explained for an example in which five subcoils 810 are provided, the number of the subcoils is not limited to this number.

For example, there may be three of the first subcoil 810A, second subcoil 810B, and fourth subcoil 810D. In this case, the first subcoil 810A and second subcoil 810B are adjusted in the same manner as that used for the subcoil 410 of the first embodiment.

In this embodiment, the magnetic coupling pattern of the first subcoil 810A, second subcoil 810B, and third subcoil 810C is not limited to that of the aforementioned example. Various kinds of patterns similar to those of the second embodiment can be used.

The modifications of the first embodiment such as those for type of circuit element used for the low impedance signal processing circuit 830, resonance frequency used at the time of adjustment of circuit elements, disposition position of each subcoil 810, presence or absence of coupling inductor, shape of loop, and size of each subcoil 810 can also be applied to this embodiment.

Fourth Embodiment

Hereafter, the fourth embodiment of the present invention will be explained. In the aforementioned embodiments, an array coil in which adjacent subcoils are magnetically coupled to expand sensitivity area at the time of signal reception is used for the receiving RF coil 161. However, in this embodiment, such an array coil is used for the transmitting RF coil 151.

The MRI apparatus of this embodiment basically has the same configuration as that of the MRI apparatus 100 of the first embodiment. Hereafter, this embodiment will be explained by focusing the explanation on configurations different from those of the first embodiment.

As described above, in this embodiment, an array coil (transmitting RF coil) constituted by a plurality of subcoils 410 is used for the transmitting RF coil 151 instead of the birdcage type RF coil 300 of the aforementioned embodiments.

Figure 18:
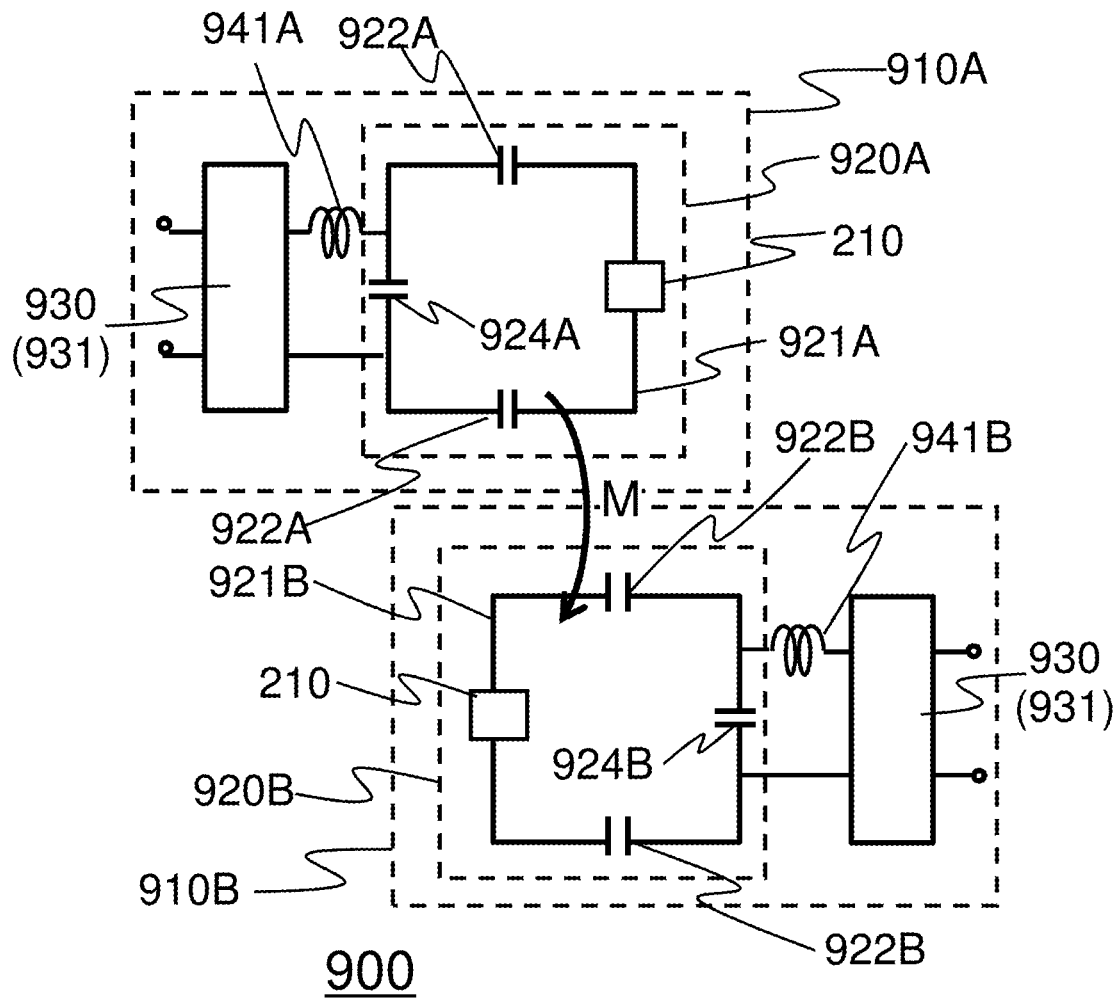
FIG. 18a is an explanatory drawing for explaining the transmitting array coil of the fourth embodiment.
FIG. 18b is an explanatory drawing for explaining the magnetic coupling between transmission and reception coils-preventing circuit of the fourth embodiment.
Figure 18:
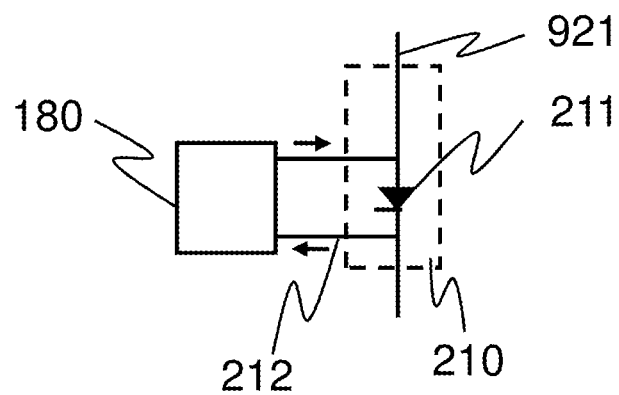

FIG. 18a is a drawing for explaining a transmitting array coil 900 used as the transmitting RF coil 151 of this embodiment. The transmitting array coil 900 of this embodiment comprises a plurality of subcoils 910, like the array coil 400 of the first embodiment. The following explanation will be made for an example in which the transmitting array coil 900 comprises two of subcoils 910A and 910B. However, the number of the subcoils 910 is not limited to this number.

Each subcoil 910 has basically the same configuration as that of the subcoil 410 of the first embodiment. However, the loop coil part 920 is connected via a magnetic coupling-adjusting part 941, not to the low input impedance signal processing circuit 430, but to a low output impedance signal processing circuit 930. The following explanation will be made for a case where an RF amplifier of low output impedance (low output impedance signal amplifier) 931 is provided as the low (output) impedance signal processing circuit 930 as an example.

The transmitting array coil 900 also comprises the magnetic coupling between transmitting and receiving coils-preventing circuit 210 as a magnetic coupling between transmission and reception coils-preventing circuit for preventing magnetic coupling between the transmitting RF coil 151 and the receiving RF coil 161.

FIG. 18b is a drawing for explaining the configuration and connection of the magnetic coupling between transmitting and receiving coils-preventing circuit 210. The magnetic coupling between transmitting and receiving coils-preventing circuit 210 is the same as the magnetic coupling between transmitting and receiving coils-preventing circuit 210 shown in FIG. 4b, and operates in the same manner as that described above. The following explanation will be focused on only the operation at the time of transmission of radio frequency magnetic field, and it is supposed that the receiving RF coil 161 is opened.

The adjustment of the circuit elements is also performed basically in the same manner as that for the array coil 400 of the first embodiment. The adjustment is performed by adjustments of a series capacitor 922 serially inserted into a loop 921 of a loop coil part 920A, a parallel capacitor 924 inserted in parallel, and the magnetic coupling-adjusting part 941.

Details of the operation of the transmitting array coil 900 of this embodiment will be explained.

Since the low output impedance signal amplifiers 931 show low impedance with respect to each of the subcoils 910 that constitute the transmitting the array coil 900 at the time of signal transmission, the equivalent circuit thereof is similar to the equivalent circuit 600 shown in FIG. 7a.

Therefore, each subcoil 910 of the transmitting array coil 900 forms the same current distribution as that of each subcoil 410 of the array coil 400 of the first embodiment, and resonates at, for example, the nuclear magnetic resonance frequency of hydrogen at a static magnetic field intensity of 3 T (Tesla), 124 MHz.

As explained above, the MRI apparatus 100 of this embodiment comprises a static magnetic field formation part for forming a static magnetic field, a gradient magnetic field formation part for forming a gradient magnetic field, a radio frequency magnetic field generation part for generating a radio frequency magnetic field, a transmitting coil 151 for irradiating the radio frequency magnetic field on a test subject, a receiving coil 161 for detecting a magnetic resonance signal from the test subject, and an image reconstruction part for reconstructing an image from the detected magnetic resonance signal. The transmitting coil 151 is a radio frequency coil (transmitting array coil 900) comprising the first subcoil 910A that has the first loop coil part 920A consisting of a conductor, and can transmit and receive a magnetic resonance signal, and the second subcoil 910B that has the second loop coil part 920B consisting of a conductor, and can transmit and receive a magnetic resonance signal, in which the first subcoil 910A is disposed and adjusted so that resonance frequency of the first subcoil 910A alone is different from nuclear magnetic resonance frequency as frequency of the magnetic resonance signal as the object for transmission and reception, and the first subcoil 910A magnetically couples with the second subcoil 910B to form circling electric current paths in the loop 921A of the first loop coil part 920A, and the loop 921B of the second loop coil part 920B, and it resonates at the nuclear magnetic resonance frequency. The transmitting coil 151 and the receiving coil 161 comprise magnetic coupling-preventing circuits 210 and 220 that prevent magnetic coupling between the transmitting coil 151 and the receiving coil 161, respectively.

As described above, since the subcoils 910 that constitute the transmitting array coil 900 of this embodiment each resonate at a desired frequency (for example, 124 MHz), the transmitting array coil can efficiently transmit RF signals. At the same time, the first loop 921A of the first loop coil part 920A of the first subcoil 910A couples with the second loop 921B of the second loop coil part 920B of the second subcoil 910B by magnetic coupling. Therefore, it can be regarded that the first subcoil 910A has a large coil loop, and RF transmission feasible region is expanded. Since the first subcoil 910A has a sensitivity profile like, for example, that of a butterfly coil, deep part sensitivity can be obtained.

The second subcoil 910B does not couple with the first loop 921A of the first loop coil part 920A of the first subcoil 910A, and has a sensitivity area different from that of the first subcoil 910A. Therefore, the transmitting coil functions as a multi-channel transmitting coil.

Therefore, the transmitting array coil 900 of this embodiment can be realized as a coil having a wide RF transmitting region with maintaining the number of channels. Further, this characteristic is realized by disposition of the subcoils 910, and adjustment of values of circuit elements, the structure is not complicated, either.

The modifications of the first embodiment such as those for type of circuit element used for the low impedance signal processing circuit, resonance frequency used at the time of adjustment of circuit elements, disposition position of each subcoil, presence or absence of coupling inductor, shape of loop, size of each subcoil, and magnetic coupling pattern can also be applied to this embodiment.

Although the embodiments of the present invention have been explained with reference to application thereof to the MRI apparatus 100 comprising horizontal magnetic field type magnet 110 as an example, the present invention can also be applied to the MRI apparatus 101 of the vertical magnetic field type as described above. That is, it becomes possible to use a multi-channel array coil using a plurality of surface coils (for example, the array coil 800 shown in FIG. 17) also in the MRI apparatus 101 of the vertical magnetic field type, which use is difficult in such a conventional MRI apparatus. The degree of freedom for design of array coil is thereby increased also for the MRI apparatus 101 of the vertical magnetic field type, and sensitivity can be increased. Because of the increase of the degree of freedom, the array coil can also be simplified, and therefore a lightweight array coil can also be designed. The burden imposed on operator and imaging subject (test subject) can also be thereby reduced.

DESCRIPTION OF NUMERICAL NOTATIONS

090: Coordinate system
100: MRI apparatus
102: Table
103: Test subject
110: Magnet
111: Magnet
121: Shim coil
122: Shim power supply
131: Gradient coil
132: Storage medium
132: Gradient magnetic field power supply
140: Sequencer
151: Transmitting RF coil
152: Radio frequency magnetic field generator
161: Receiving RF coil
162: Receiver
170: Computer
171: Display
180: Magnetic coupling-preventing circuit drive
210: Magnetic coupling between transmitting and receiving coils-preventing circuit
211: PIN diode
212: Signal wire for control
220: Magnetic coupling between transmitting and receiving coils-preventing circuit
220m: Magnetic coupling between transmitting and receiving coils-preventing circuit
221: PIN diode
221m: Cross diode
222: Inductor
223: Signal wire for control
300: Birdcage type RF coil
301: Linear conductor
302: End conductor
303: Capacitor
311: Input port
312: Input port
400: Array coil
401: Array coil
402: Saddle-shaped array coil
403: Solenoid-shaped array Coil
404: Array coil
410: Subcoil
420: Loop coil part
421: Loop
422: series capacitor
423: Capacitor
424: Capacitor
424: Parallel capacitor
430: Low impedance signal processing circuit
431: Low input impedance signal amplifier
441: Magnetic coupling-adjusting part
451: Coupling inductor
462: Coil part
463: Coil part
500: Parallel resonant circuit
501: Capacitor
502: Inductor
511: Sensitivity map
512: Sensitivity map
513: Sensitivity map
514: Sensitivity map
521: Sensitivity profile
522: Sensitivity profile
531: Sensitivity profile
532: Sensitivity profile
533: Sensitivity profile
534: Sensitivity profile
600: Equivalent circuit
601: Equivalent circuit
602: Equivalent circuit
604: Equivalent circuit
605: Equivalent circuit
606: Equivalent circuit
621: Inductor
622: Series capacitor
624: Parallel capacitor
626: Inductor
627: Inductor
632: Impedance
641: Adjustment inductor
700: Array coil
710: Subcoil
720: Loop coil part
730: Low impedance signal processing circuit
800: Array coil
810: Subcoil
820: Loop coil part
822: Series capacitor
823: Series capacitor
824: Parallel capacitor
830: Low impedance signal processing circuit 841: Adjustment inductor
900: Transmitting array coil
910: Subcoil
920: Loop coil part
921: Loop
930: Low impedance signal processing circuit
931: Low output impedance signal amplifier

The invention claimed is:
1. A radio frequency coil comprising:
a first subcoil that has a first loop coil part consisting of a conductor, and is configured to transmit and receive a magnetic resonance signal,
a second subcoil that has a second loop coil part consisting of a conductor, and is configured to transmit and receive a magnetic resonance signal,
wherein the first subcoil is disposed such that a resonance frequency of the first subcoil alone is different from a nuclear magnetic resonance frequency, which is a frequency of a magnetic resonance signal of an object for transmission and reception, and
wherein the first subcoil magnetically couples with the second subcoil to form circling electric current paths in a loop of the first loop coil part and a loop of the second loop coil part, and to resonate at the nuclear magnetic resonance frequency.
2. The radio frequency coil according to claim 1,
wherein the second subcoil is disposed such that a resonance frequency of the second subcoil alone is different from the nuclear magnetic resonance frequency, and
wherein the second subcoil magnetically couples with the first subcoil to form circling electric current paths in a loop of the first loop coil part and a loop of the second loop coil part, and to resonate at the nuclear magnetic resonance frequency.
3. The radio frequency coil according to claim 1,
wherein the first subcoil further comprises a first magnetic coupling-adjusting part that connects the first loop coil part and a first low impedance signal processing circuit to which the first subcoil is connected,
wherein the first loop coil part comprises:
a first series capacitor that is serially inserted with respect to an inductor component of the loop,
a first parallel capacitor that is serially inserted with respect to the inductor component, and makes the first loop coil part to be a parallel resonant circuit,
wherein the second subcoil further comprises a second magnetic coupling-adjusting part that connects the second loop coil part and a second low impedance signal processing circuit to which the second subcoil is connected,
wherein the second loop coil part comprises:
a second series capacitor that is serially inserted with respect to inductor component of the loop,
a second parallel capacitor that is serially inserted with respect to the inductor component, and makes the second loop coil part to be a parallel resonant circuit,
wherein the first magnetic coupling-adjusting part comprises at least one of a capacitor and an inductor as a first adjustment circuit element,
wherein the second magnetic coupling-adjusting part comprises at least one of a capacitor and an inductor as a second adjustment circuit element, and
wherein the first subcoil and the second subcoil are adjusted by adjusting values of the first adjustment circuit element, the second adjustment circuit element, the first series capacitor, the second series capacitor, the first parallel capacitor, and the second parallel capacitor.
4. The radio frequency coil according to claim 1,
wherein the first subcoil and the second subcoil are disposed in at such positions that the first subcoil and the second subcoil magnetically couple with each other.
5. The radio frequency coil according to claim 1,
wherein the first subcoil further comprises a first coupling inductor,
wherein the second subcoil further comprises a second coupling inductor, and
wherein the first subcoil and the second subcoil magnetically couple with each other with the first coupling inductor and the second coupling inductor.
6. The radio frequency coil according to claim 1,
wherein the radio frequency coil further comprises a third subcoil that has a third loop coil part consisting of a conductor, and can transmit and receive a magnetic resonance signal, and
wherein the third subcoil is disposed and adjusted so that a resonance frequency of the third subcoil alone is different from the nuclear magnetic resonance frequency and, and the third subcoil magnetically couples with the second subcoil to form circling electric current paths in a loop of the third loop coil part and a loop of the second loop coil part, and to resonate at the nuclear magnetic resonance frequency.
7. The radio frequency coil according to claim 1,
wherein the radio frequency coil further comprises a fourth subcoil that has a fourth loop coil part consisting of a conductor, and is configured to transmit and receive a magnetic resonance signal,
wherein the fourth subcoil is disposed so that the fourth loop coil part has overlapping regions that overlap with the first loop coil part and the second loop coil part, respectively, and
wherein areas of the overlapping regions are determined so that the fourth subcoil does not magnetically couple with the first subcoil and the second subcoil.
8. The radio frequency coil according to claim 1,
wherein the first subcoil and the second subcoil are connected to a low input impedance signal processing circuit, respectively, and function as a receiving coil that receives the magnetic resonance signal.
9. The radio frequency coil according to claim 1,
wherein the first subcoil and the second subcoil are connected to a low output impedance signal processing circuit, and function as a transmitting coil that transmits the magnetic resonance signal.
10. A magnetic resonance imaging apparatus comprising:
a static magnetic field formation part for forming a static magnetic field,
a gradient magnetic field formation part for forming a gradient magnetic field,
a radio frequency magnetic field generation part for generating a radio frequency magnetic field,
a transmitting coil for irradiating the radio frequency magnetic field on a test subject,
a receiving coil for detecting a magnetic resonance signal from the test subject, and
an image reconstruction part for reconstructing an image from the detected magnetic resonance signal, wherein:
at least one of the transmitting coil and the receiving coil is the radio frequency coil according to claim 1, and the transmitting coil and the receiving coil each comprise a magnetic coupling-preventing circuit that prevents magnetic coupling between the transmitting coil and the receiving coil.

* * * * *